United States Patent [19]
Rexroth

[11] Patent Number: 5,217,478
[45] Date of Patent: Jun. 8, 1993

[54] ARTHROSCOPIC SURGICAL INSTRUMENT DRIVE SYSTEM

[75] Inventor: Fred Rexroth, Dunedin, Fla.

[73] Assignee: Linvatec Corporation, Largo, Fla.

[21] Appl. No.: 16,140

[22] Filed: Feb. 18, 1987

[51] Int. Cl.$^5$ .............................................. A61B 17/20
[52] U.S. Cl. ...................................... 606/180; 606/172
[58] Field of Search ............... 128/303.1, 303 R, 305, 128/1 R, 898, 897; 433/99, 27; 200/5 A, 159; 310/68 A, 68 B; 604/110, 111; 606/172, 180

[56] References Cited

U.S. PATENT DOCUMENTS

| | | | |
|---|---|---|---|
| Re. 30,923 | 5/1982 | Durkee et al. | 200/5 A |
| 1,201,365 | 10/1916 | Shelton | 310/68 A |
| 1,977,263 | 10/1934 | Campbell | 433/99 |
| 2,637,824 | 5/1953 | Kessel | 310/68 A |
| 2,754,464 | 6/1956 | Wizenez et al. | 310/68 B |
| 3,346,958 | 10/1967 | Sinatra et al. | 433/99 |
| 3,427,720 | 2/1969 | Berman et al. | 433/99 |
| 3,673,357 | 6/1972 | Molchan | 200/5 A |
| 3,699,294 | 10/1972 | Sudduth | 200/5 A |
| 3,734,099 | 5/1973 | Bender et al. | 128/305 |
| 3,848,336 | 11/1974 | Copeland | 433/99 |
| 3,921,298 | 11/1975 | Fattaleh | 433/99 |
| 3,959,883 | 6/1976 | Walls et al. | 433/99 |
| 4,066,851 | 1/1978 | White et al. | 200/5 A |
| 4,066,855 | 1/1978 | Zenk | 200/5 A |
| 4,104,728 | 8/1978 | Kasubuchi | 200/5 A |
| 4,128,889 | 12/1978 | Ojima et al. | 200/5 A |
| 4,216,968 | 8/1980 | Yeeda | 200/5 A |
| 4,220,815 | 9/1980 | Gibson et al. | 200/5 A |
| 4,274,414 | 6/1981 | Johnson et al. | 128/305 |
| 4,276,024 | 6/1981 | Warren | 433/99 |
| 4,320,716 | 3/1982 | Haddad | 128/305 |
| 4,320,767 | 3/1982 | Villa-Read | 128/680 |
| 4,321,441 | 3/1982 | Thornburg | 200/5 A |
| 4,360,716 | 11/1982 | Fiorella | 200/5 A |
| 4,449,023 | 5/1984 | Hilhorst et al. | 200/5 A |
| 4,470,414 | 9/1984 | Imagawa et al. | 128/303.1 |
| 4,608,215 | 8/1986 | Gonczy et al. | 264/61 |
| 4,702,738 | 10/1987 | Spencer | 604/263 |
| 4,705,038 | 11/1987 | Sjostrom et al. | 126/305 |

FOREIGN PATENT DOCUMENTS

| | | | |
|---|---|---|---|
| 1036465 | 8/1958 | Fed. Rep. of Germany | 433/99 |
| 1192365 | 5/1965 | Fed. Rep. of Germany | 433/99 |
| 2712734 | 9/1978 | Fed. Rep. of Germany | 433/99 |
| 2840623 | 5/1979 | Fed. Rep. of Germany | 433/99 |
| 3122062 | 2/1982 | Fed. Rep. of Germany | 433/99 |
| 2304955 | 10/1976 | France | 433/99 |
| 373518 | 1/1964 | Switzerland | 433/99 |
| 2078006 | 12/1981 | United Kingdom | 433/99 |
| 2093353 | 9/1982 | United Kingdom | 128/305 |

OTHER PUBLICATIONS

Dentsphy-Cavitron Litturature: "Powermatic TM Ultrasonic dental Unit" 1976.

Primary Examiner—David B. Shay

[57] ABSTRACT

A motor-driven surgical instrument having particular use in arthroscopic procedures has its drive motor operation controllable entirely from a switch cluster mounted on the instrument handpiece. The switch cluster is curved to substantially follow the circumferential profile of the handpiece and thereby avoid large platforms or projections that would add to the weight and bulk of the handpiece and destroy its balance. The switches in the cluster are arranged to minimize the movement of a surgeon's finger in quickly moving from a speed or direction control switch to an on/off switch. A unique arcuate printed circuit board having a small radius of curvature is employed as part of the switch cluster and is able to withstand the high temperatures to which the handpiece is exposed during sterilization between procedures. Disposable, single-use cutting blades are individually coded to provide a sensible parameter representing the optimum operating speed range of the cutting blade. This parameter is sensed by the handpiece to provide a control signal which both establishes the optimum motor speed range and provides a visible indication of the established range. In this manner the instrument is able to avoid relatively heavy coded adapters employed in the prior art to provide interface between the cutting blade and the handpiece.

9 Claims, 11 Drawing Sheets

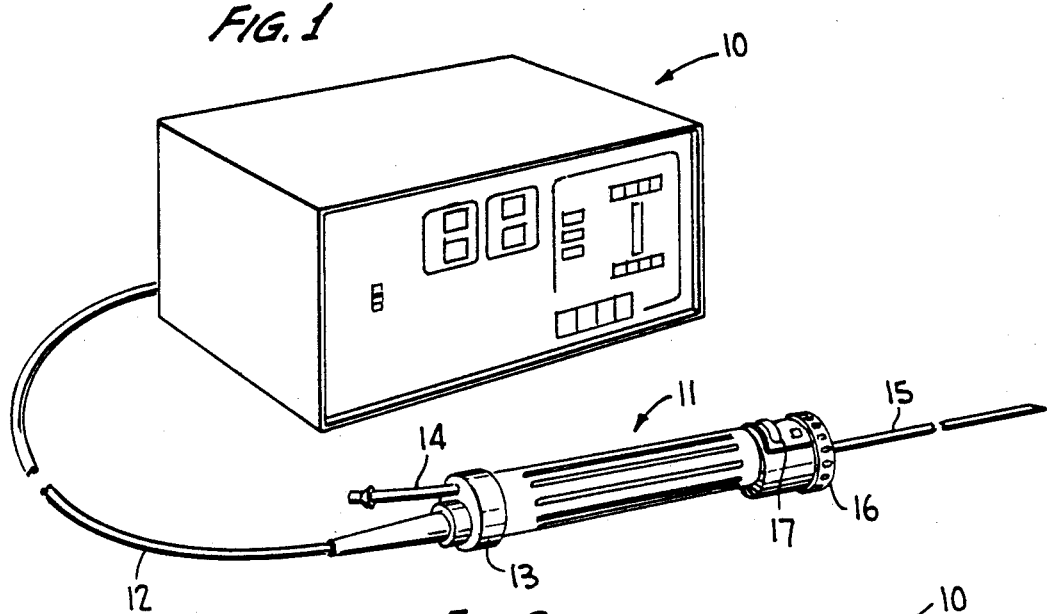
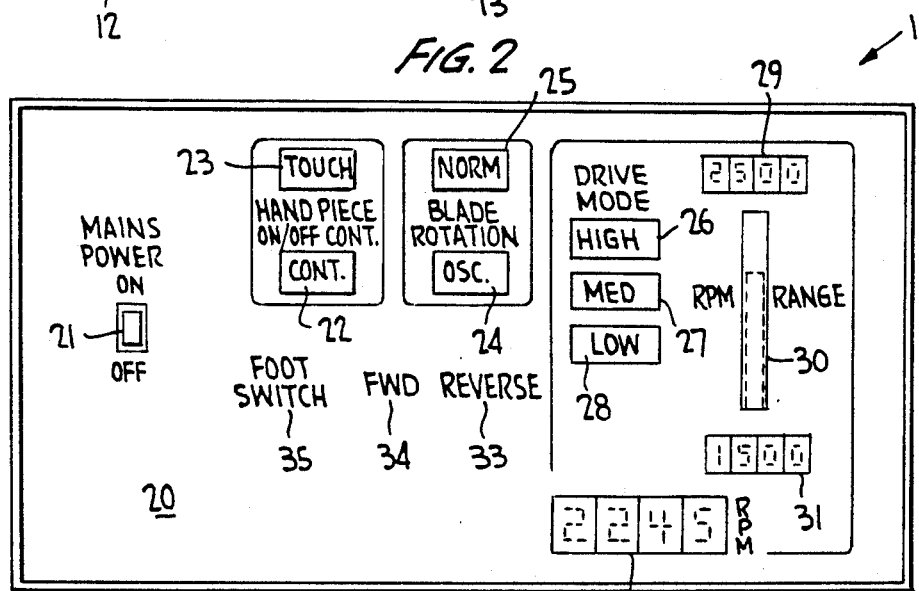
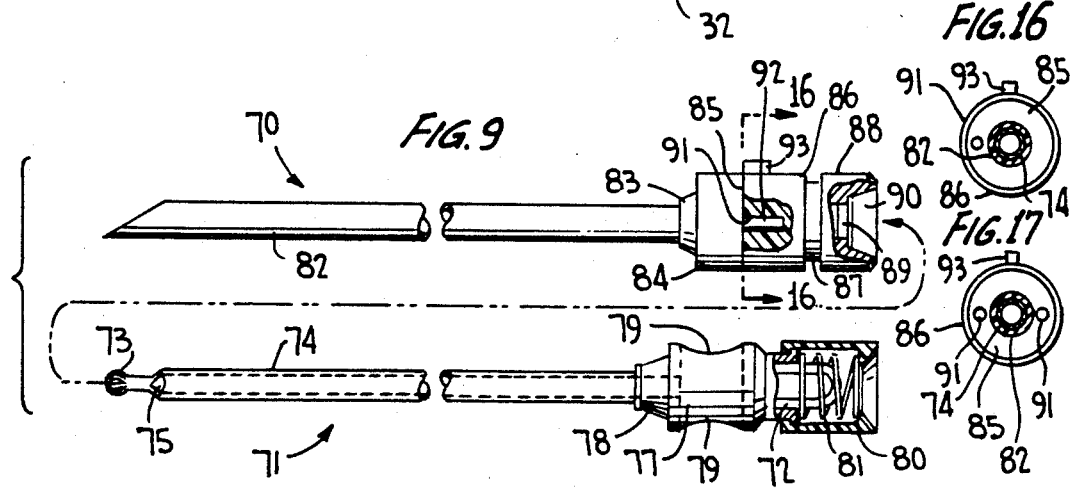

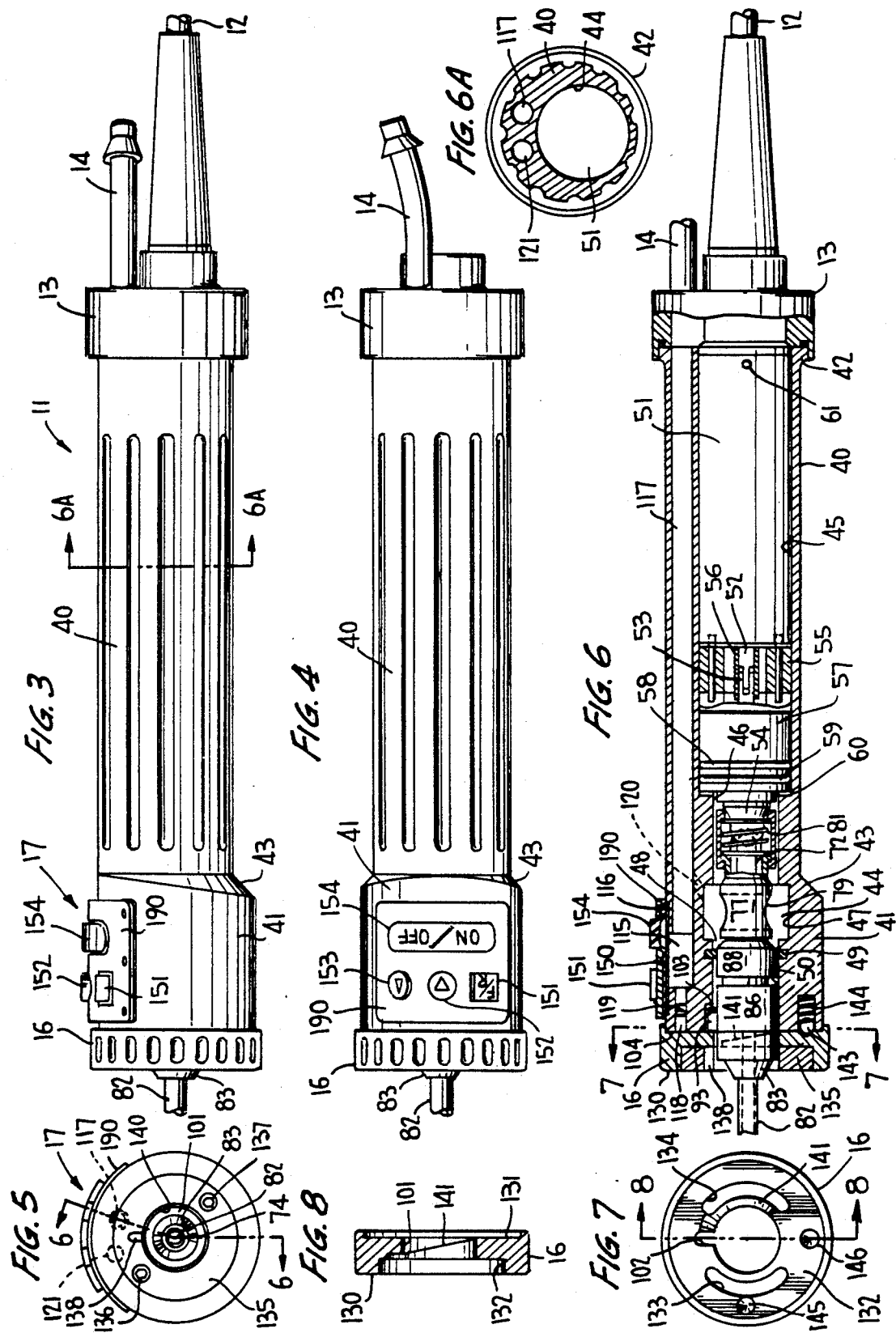

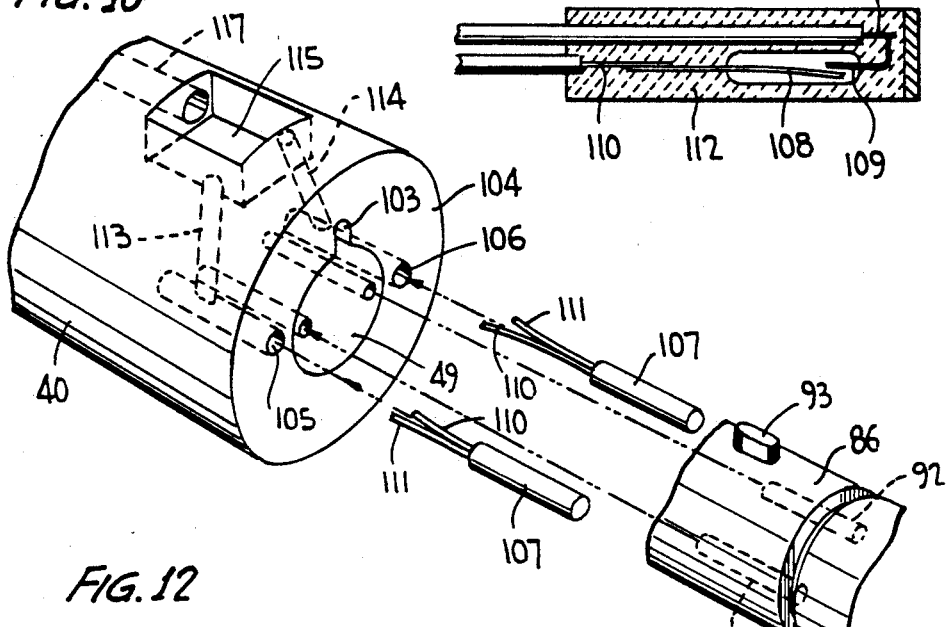

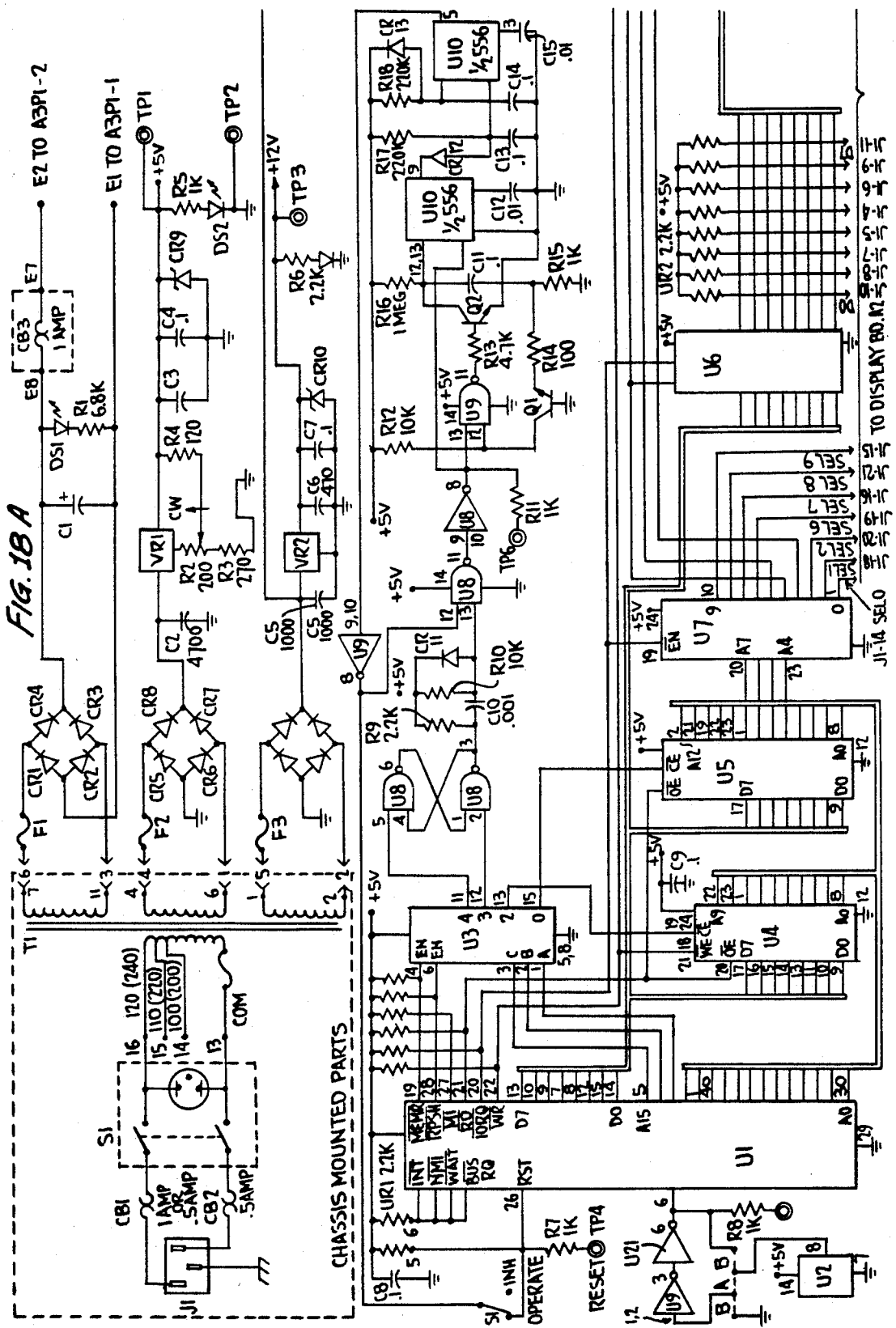
FIG. 1B A

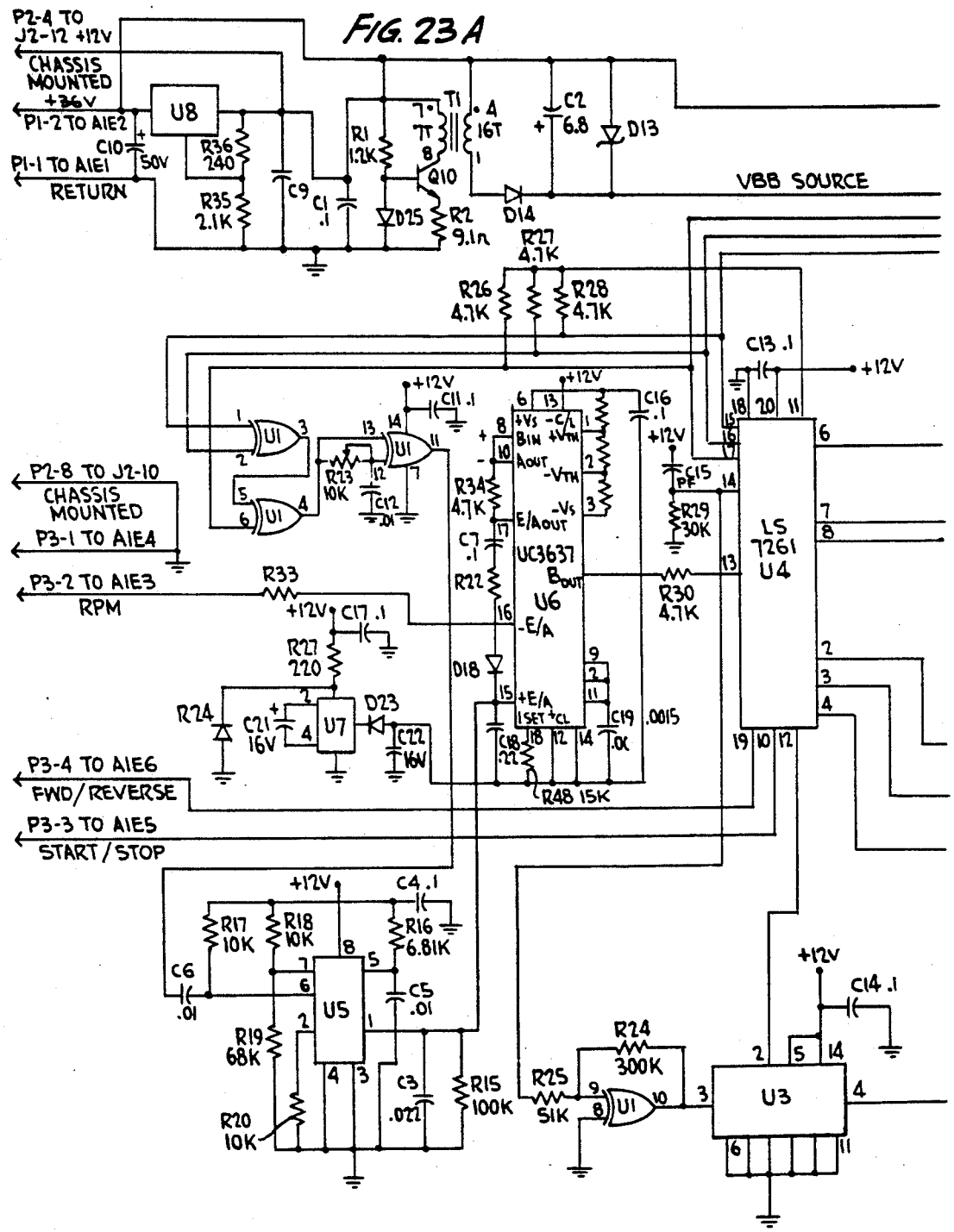

ARTHROSCOPIC SURGICAL INSTRUMENT DRIVE SYSTEM

BACKGROUND OF THE INVENTION

1. Technical Field

The present invention relates to surgical instruments and, more particularly, to instruments having rotatable motor-driven arthroscopic cutting blades capable of removing fibrous tissue lying between articulate surfaces in and around joints of the body. In addition, the instrument of the present invention can be used to balance meniscal rims and to evacuate excised tissue.

2. Discussion of the Prior Art

A typical prior art arthroscopic surgical instrument is disclosed in U.S. Pat. Nos. 4,203,444 (Bonnell et al) and 4,274,414 (Johnson et al). The disclosed instruments are elongated handpieces serving as a housing for a motor which rotatably drives a cutting blade projecting longitudinally from the forward end of the handpiece. The blade is disposed in an apertured sheath or outer tube through which excised tissue material is aspirated via suction applied through the handpiece. Controls for the motor (i.e., on/off, speed control, etc.) are located at a console and connected to the motor via a cable interconnecting the console with the handpiece.

Surgical instruments of the type described must be fabricated of material capable of withstanding autoclave temperatures (i.e., in excess of 270 degrees Fahrenheit) so that the instrument may be sterilized between surgical procedures. It is recognized in the prior art that cutting blades may be designed to be disposable (i.e., the blades are used for a single procedure and then discarded) so as to avoid the requirement of blade sterilization between procedures. However, the handpiece and the components housed therein must be repeatedly sterilized. On the other hand, the control console, which houses electrical circuitry and controls, is not required to be sterilized between uses. As a consequence, a surgeon cannot operate the console controls during a surgical procedure and must rely on an assistant to do so.

It is also recognized in the prior art that certain cutting blades, designed for specific types of surgical procedures, operate optimally within specified ranges of rotational speed. In some commercially-available systems a switch is provided on the control console to permit the operator to select a speed range that is consistent with the cutting blade to be used. A further control at the console permits the operator to select the desired speed within the selected range. A more recent development (made commercially available by Dyonics, Inc., of Andover, Mass. as the "Advanced Arthroscopic Surgical System") automatically sets the speed range appropriate for the selected cutting blade. This is achieved by providing three different cutting blade adapters (i.e., one adapter for each of the possible speed ranges) by which the cutting blade may be operably engaged with the handpiece. The adapters are coded for the desired speed range by means of one or more magnets at specified locations in the adapters. Reed switches in the handpiece ar actuated by respective magnets and transmit the speed range control code information to the console to establish the correct speed range. A manual control at the console permits selection of particular speeds within the established range.

As noted above, prior art instruments of the type described have controls at the console which cannot be operated by the surgeon during a procedure without compromising sterilization. It is desirable, therefore, to provide all of the controls on the handpiece. However, there are a number of obstacles which have precluded placing the controls on the handpiece. Specifically, the entire handpiece must be capable of withstanding the temperatures experienced in an autoclave during sterilization. In addition, the controls should not increase the bulk of the handpiece, particularly in its transverse dimension, since increased bulk renders the handpiece unwieldy to manipulate during surgical procedures. Finally, the controls must be located in a convenient manner so as to permit the surgeon to quickly and easily operate each control, preferably with the one hand that holds the handpiece. Prior to the present invention, the prior art has been unable to overcome this combination of obstacles.

In addition, although it is desirable to provide for automatic setting of speed ranges to optimize specific blade operation, the prior art approach has certain disadvantages. In particular, the coded adapter is an additional part of the system which must be capable of withstanding autoclaving temperatures. Consequently, the adapter is relatively heavy and adds significantly to the overall weight of the handpiece. This adversely affects manipulability of the handpiece during surgical procedures. It is desirable, therefore, to provide for automatic speed range selection while eliminating the extra adapter part.

OBJECTS AND SUMMARY OF THE INVENTION

It is therefore an object of the present invention to provide a surgical instrument of the type described wherein controls are provided at the handpiece to permit the entire operation of the instrument to be controlled from the handpiece without adding significant weight or volume to the handpiece.

It is another object of the present invention to provide a surgical instrument of the type described which includes automatic speed range selection without requiring a separate adapter part for connecting the cutting blade to the handpiece.

A further object of the invention is to provide a disposable cutting blade for a surgical instrument of the type described, which blade can be used with both the handpiece of the present invention and with the above-described prior art instruments having speed range adapters for connecting the blade to the handpiece.

It is yet another object of the present invention to provide a switch cluster on a handpiece of an arthroscopic surgical instrument wherein the cluster does not project transversely significantly beyond the contour of the handpiece, wherein the individual switches in the cluster are oriented to be easily accessed by the surgeon's hand in which the handpiece is held, and wherein the switch cluster and associated circuit in the handpiece are capable of withstanding autoclave temperatures.

A still further object of the present invention is to provide a surgical instrument of the type described wherein automatic setting of the optimal speed range for each disposable cutting blade is achieved by coding the disposable cutting blades themselves rather than by employing a separate coded and reusable adapter part for connecting the cutting blade to the handpiece.

In accordance with the present invention an arthroscopic surgical instrument can be controlled from a switch cluster located proximate the forward end of a handpiece. The switch cluster includes a plurality of pushbutton switches and is arrayed arcuately to correspond to the curvature of the handpiece periphery. An arcuate printed circuit board is disposed within the handpiece and closely spaced from the switch cluster so that actuation of each switch bridges a corresponding pair of printed circuit contacts. Both the arcuate switch cluster and the arcuate printed circuit board are constructed to withstand autoclave temperatures to which the entire handpiece assembly is subjected when sterilized. Importantly, the small radius of curvature required for the printed circuit board renders the choice of material of paramount importance in order to prevent the board from becoming brittle when exposed to autoclaving temperatures.

The switch cluster includes four pushbuttons for: (1) controlling motor direction; (2) increasing motor speed; (3) decreasing motor speed; and (4) actuating and deactuating the motor (i.e., on/off). In the optimum arrangement, switches (1), (2) and (3) are disposed proximate the forward end of the handpiece and are aligned along an arcuate path extending along the handpiece circumference. The on/off switch (4) is disposed immediately longitudinally behind the other three switches and is elongated arcuately. The surgeon can actuate each of the switches using a single finger of the hand in which the handpiece is supported. The arcuately elongated on/off switch permits the motor to be rapidly deactuated with minimal movement of the surgeon's actuation finger.

In order to automatically select the optimal motor speed range for each cutting blade, mutually interactive coding and decoding elements are disposed directly in the cutting blade and the handpiece, respectively. In the preferred embodiment, magnets are disposed in the cutting blade and reed switches are disposed in the handpiece to effect automatic speed range control in a manner similar to the prior art described above; however, and importantly, control is effected without the need for an extra adapter part. An advantage of the magnet and reed switch arrangement is that it permits the cutting blades to be usable with the handpiece of the present invention while also mechanically fitting into the adapter of the prior art handpiece. However, other cutting blade-handpiece coding arrangements may be employed, such as: mechanical projections on the cutting blade hubs positioned to actuate respective pressure-sealed switches in the handpiece; projections on the blade hubs blocking respective light paths in light-actuated circuits in the handpiece; etc. Whichever coding arrangement is used, the sensing components in the handpiece must be sealed so as not to be damaged during autoclaving.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 1 is a view in perspective of a control console and handpiece unit of a preferred embodiment of the present invention;

FIG. 2 is a view in elevation of the front panel of the control console of FIG. 1;

FIG. 3 is a side view in elevation of the handpiece unit of FIG. 1;

FIG. 4 is a top view in plan of the handpiece unit of FIG. 3;

FIG. 5 is an end view in elevation of the handpiece unit of FIG. 3;

FIG. 6 is a view in longitudinal section taken along lines 6—6 of FIG. 5;

FIG. 6A is a view in transverse section taken along lines 6A—6A of FIG. 3;

FIG. 7 is a view of the rearward-facing surface of the locking ring secured to the handpiece unit as viewed along lines 7—7 of FIG. 6;

FIG. 8 is a view in section of the locking ring taken along lines 8—8 of FIG. 7;

FIG. 9 is an exploded side view in elevation and partial section of a cutting blade assembly employed in conjunction with the handpiece unit of FIG. 6;

FIG. 10 is a diagramatic illustration of the manner in which the speed range coding of a cutting blade is detected by the handpiece unit in accordance with the principles of the present invention;

FIG. 11 is a view in longitudinal section of a reed switch employed in the handpiece unit to detect magnetic speed range coding present in cutting blade assemblies inserted into the handpiece;

FIG. 12 is a top view in plan of the control switch cluster provided on the handpiece unit of the present invention;

FIG. 13 is a view in transverse section taken along lines 13—13 of FIG. 12 and showing three of the control switches provided as part of the control switch cluster;

FIG. 14 is a view in perspective of the printed circuit board employed as part of the switch cluster assembly in the handpiece;

FIG. 15 is a view in transverse section taken along lines 15—15 of FIG. 12 and showing a fourth switch provided as part of the handpiece switch cluster;

FIG. 16 is a view in section of the cutting blade assembly taken along lines 16—16 of FIG. 9;

FIG. 17 is a view similar to that of FIG. 16 for a different cutting blade assembly coded to have a different optimal operating speed than the cutting blade assembly illustrated in FIG. 16;

DESCRIPTION OF THE PREFERRED EMBODIMENT

Figure 18B:
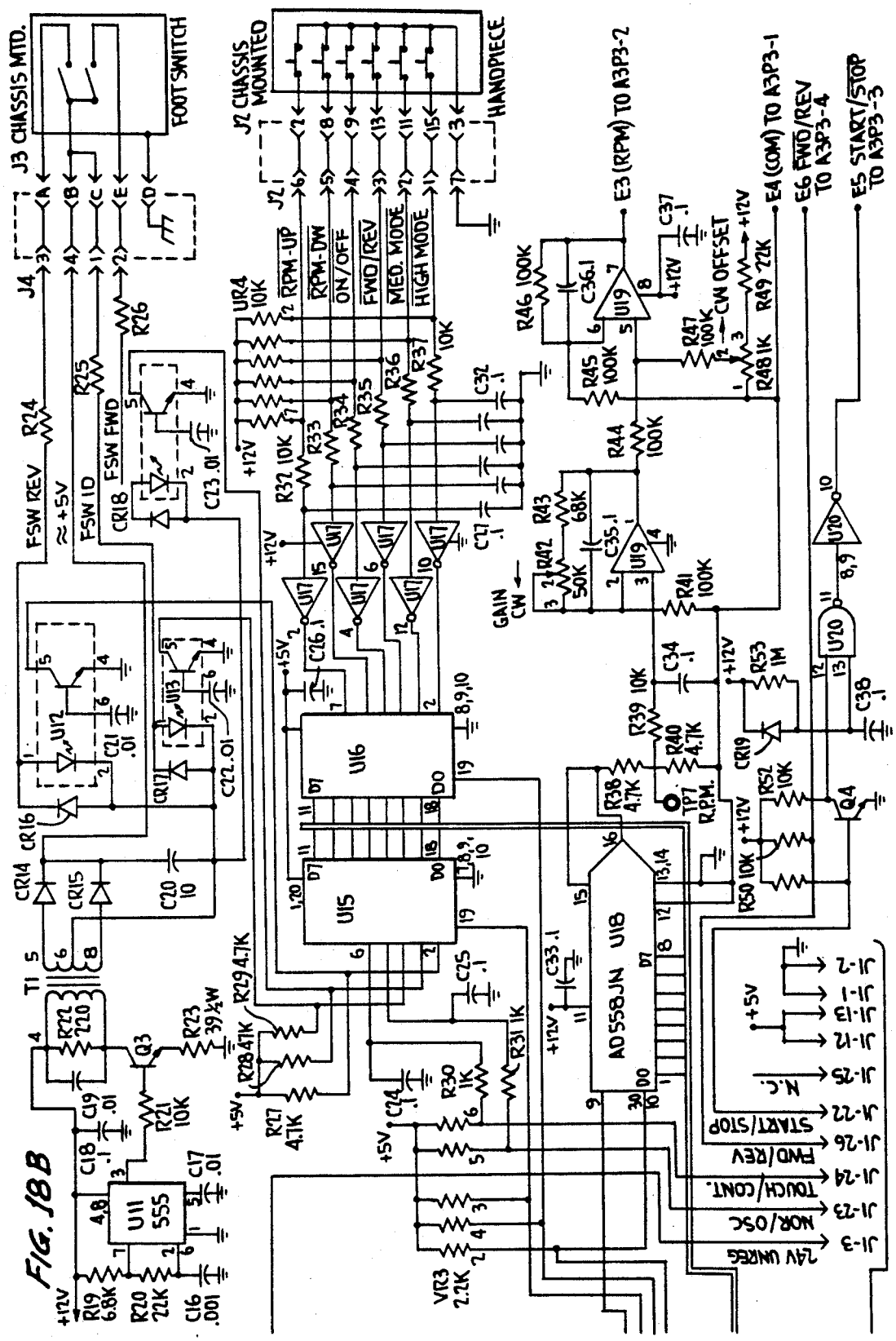
FIG. 18 is a detailed schematic diagram of the electronic components employed on the control board located in the control console.

Referring specifically to FIG. 1 of the accompanying drawings, a surgical instrument constructed according to the present invention includes a control console 10 electrically interconnected to a surgical handpiece 11 via a flexible drive unit cable 12. Cable 12 terminates at one end in a plural-conductor connector (not shown) that is received in a receptacle (not shown) secured at the rear or side of console 10. The other end of cable 12 terminates in an end cap 13 located at the proximal or rearward end of the handpiece 11. Also extending from the handpiece end cap 13 is a suction tube 14 that communicates with the handpiece interior and serves, in a conventional manner, to conduct fluid from the handpiece to a vacuum source (not shown). Typically, a control valve is disposed in the suction line intermediate tube 14 and the vacuum source to provide control over the aspiration of fluid from the surgical site and through the handpiece interior. A cutting blade 15 projects from a locking ring 16 disposed at the forward or distal end of the handpiece 11. The handpiece is generally cylindrical and the cutting blade is oriented to project substantially coaxially along the central longitudinal axis of the locking ring 16. A cluster 17 of control switches is disposed in an arcuate array proximate the forward end of the handpiece 11, the cluster being curved to correspond to the circumferential profile of the handpiece.

As illustrated in greater detail in FIG. 2, control console 10 has a front panel 20 with a number of controls and indicators. Specifically, a mains power switch 21 of the rocker type permits application and removal of primary power to and from the system. Lighted switches 22 and 23 actuate the blade drive motor in the handpiece 11. If the continuous switch 22 is pressed and released, the drive motor rotates and the switch lights; if the switch is pressed and released again, the motor stops and the switch light is turned off. If the touch switch 23 is held depressed, the motor rotates and the switch lights; release of the switch stops the motor and turns off the switch light.

The blade rotation switches 24 and 25 control the rotation direction of the motor. When the OSC switch 24 is pressed and released, the motor changes rotation directions at pre-set intervals and the switch is lighted; the NORM switch 25 is unlighted. When the NORM switch 25 is pressed and released, the motor rotates in the direction selected at switch cluster 17 in the handpiece (as described below) and the switch is lighted; the OSC switch 26 remains unlighted.

The drive mode indicators 26, 27 and 28 are lighted to indicate when a respective motor speed range has been automatically established by the particular cutting blade 15 inserted into the handpiece (in the manner described below). The high indicator 26 lights when a high speed burr blade is inserted into the handpiece. The medium indicator 27 lights when a medium speed blade is inserted into the handpiece. The low indicator 26 lights when no blade or a low speed blade is inserted into the handpiece. In the preferred embodiment disclosed herein, the high speed range extends between 1500 and 2500 rpm; the medium range extends between 500 and 900 rpm; and the low speed range extends between 75 and 400 rpm. Indicators 26, 27 and 28 are preferably bordered in different colors corresponding to the color of the blade resulting in the automatic selection of the indicated range.

The maximum speed display 29 is a four-digit light-emitting diode (LED) display for the upper limit of the speed range currently in force. The minimum speed display 31 is a four-digit LED display for the lower limit of the speed range currently in force. The RPM range LED bar display 30 indicates the relative motor speed between the displayed minimum and maximum limits and is in the form of a lighted bar having a vertical dimension which increases with increasing motor speed. The maximum and minimum displays 29 and 31 are vertically spaced, and the range display 30 is disposed therebetween to present the range indication in a position permitting an observer to easily estimate, from the bar display, the location of the actual speed within the selected operating range. An RPM digital display 32 is a four-digit LED display of the actual motor speed. It must be noted that the word "actual" employed above to describe the speed display on bar display 30 and by digital display 32 is a misnomer. The information from which these displays are derived is the control input information originating at the console 10 and applied, by electrical signal, to the motor in the handpiece 11. In other words, the display does not reflect the measured rotational speed of the motor. However, the response of the motor to the control signal is known with sufficient accuracy to permit the control information to serve as the source of the motor speed display within the precision requirements of the system.

Indicators 33, 34 and 35 are individually illuminated status indicators. The reverse indicator 33 is illuminated when the reverse motor direction is selected at switch cluster 17 at handpiece 11; this indicator flashes on and off when the motor is rotating in reverse direction. The forward indicator 34 is illuminated when the forward motor direction is selected at switch cluster 17; this indicator also flashes when the motor is rotating in the forward direction. The footswitch indicator is illuminated when a separate foot-controlled switch (not shown) is connected to console 10. When the footswitch is so connected, the on/off, forward and reverse control switches at switch cluster 17 at the handpiece are inhibited.

Handpiece 11 is illustrated in detail in FIGS. 3-8 to which specific reference is now made. Handpiece unit 11 includes an integrally formed lightweight metal body member 40 of generally cylindrical configuration. Body member 40 is sealed at its rearward end by end cap 13 and at its forward end by locking ring 16. A slightly radially enlarged flange 42 terminates the rearward end of body member 40 as best illustrated in FIGS. 6 and 6a. The forward portion 41 of body member 40 occupies approximately twenty percent of the length of that member and is cylindrical with a somewhat larger outer-diameter than the remainder of the length of body member 40. Typically, for a body member 40 having a length of 6.57 inches, the outer diameter of forward section 41 would be 1⅜ inches, while the outer diameter of the remainder of the body member 40 would be 1.2 inches. However, forward section 41 is not disposed coaxially with respect to the remainder of body member 40. In this regard, it is helpful to consider body member 40 as having a top side and a bottom side. The top side (which is seen in plan in FIG. 4 and appears as extending along the top of the body member in FIGS. 3 and 6), is considered to be angularly centered on the line which divides switch cluster 17 into two equal transverse halves and extends longitudinally along the outside of member 40. The bottom side of body member 40 is located diametrically opposed to the top side. As best illustrated in FIGS. 3 and 6, the top side of forward section 41 is longitudinally continuous (i.e., forming a straight line) with the top side of the remainder of body member 40. At all other angular positions about the body member, forward section 41 is transversely larger than the rest of the body member 40. The transverse dimensional difference between forward section 41 and the rest of body member 40 increases with angular displacement from the top side of the body member to a maximum difference occurring at the bottom side of the member. The transition between forward section 41 and the rest of body member 40 takes the form of a chamfered surface 43 subtending an angle of approximately 45° with the longitudinal dimension of body member 40. The overall effect of the enlarged forward section 41 is a barrelled-out portion of the body member at its forward end.

As best illustrated in FIG. 6, a longitudinally-extending cylindrical bore 44, having a series of sections of different diameter, is defined entirely through body member 40. Bore 44 is concentrically disposed within forward section 41 but is displaced closer to the bottom of the remainder of body member 40. A rearward section 45 of bore 44 serves to house the drive motor for the unit and, in the described embodiment, is typically 4.475 inches long and has a diameter of 0.805 inches. Immediately forward of bore section 45 is a shorter section 46 of smaller diameter in which the motor drive shaft engages the cutting blade. Bore section 46, in the disclosed embodiment, is typically 0.805 inches long with a diameter of 0.565 inches. The next forward bore section 47 serves as an aspirator communication compartment and, in the disclosed embodiment, is typically 0.500 inches long and 0.750 inches in diameter. A short section 48 (i.e., typically 0.060 inches long, 0.565 inches in diameter) separates the aspiration communication chamber 47 from a housing section for a O-ring 49. The O-ring housing section is typically 0.110 inches long and 0.750 inches in diameter. Finally, the forward-most bore section 50 serves to receive the hub of the cutting blade. Bore section 50 is typically 0.620 inches long and 0.565 inches in diameter. The transitions between all bore sections are annular shoulders.

The motor assembly includes a cylindrical motor 51 disposed in bore section 45 and from which a rotatably driven pin 52 projects longitudinally in a forward direction into a hollow cylindrical spacer 55. Spacer 55 remains stationary and has a hollow cylindrical drive tube 56 disposed concentrically therein. Drive tube 56 is welded, tightly fit, or otherwise secured about driven pin 52 in radially spaced relation to spacer 55. Driven pin 52 has a generally rectangular transverse crosssection and is engaged in a bifurcated rearward end 53 of a drive shaft 54 which is also received in and secured to drive tube 56. Thus, when the motor is actuated, driven pin 52 is rotated and rotatably drives the drive tube 56 and drive shaft 54. A stationary bearing housing 57 is disposed immediately forward of spacer 55 to provide a bearing support for the rotatable drive shaft extending therethrough. A plurality of O-rings 58, 59 are disposed about bearing housing 57 and serve as pressure seals in a longitudinal direction in bore section 45. Additional pressure sealing is provided by a gasket 60 disposed adjacent the annular shoulder demarcating the transition between bore sections 45 and 46 and adjacent which the forward-facing end of bearing housing 57 is forcefully urged. In this regard, the housing for motor 51 is provided with a pair of diametrically opposed apertures 61 proximate the rearward end of the motor so that pins (not shown) can be inserted transversely through suitably provided openings in the handpiece body member 40 to lock the motor assembly in place against gasket 60.

The forward end of drive shaft 54 projects into bore section 46 wherein it receives a drive tang 72, projecting from the rearward end of the cutting blade, in rotatably drivable engagement. The cutting blade assembly is illustrated in greater detail in FIGS. 9, 16 and 17 to which specific reference is now made. The cutting blade assembly includes an outer member 70 and an inner member 71. The inner member includes a tube 74 with a distal cutting end 73 which, in the illustrated embodiment, is an arthroplasty burr, although other blade types (such as meniscal open end, meniscal side cutter, end cutter, trimmer, meniscus cutter, synovial resector, and full radius resector) may be employed. Each cutting blade tube 74 is hollow and has an opening 75 proximate the distal end 73 to admit excised tissue aspirated from the surgical site in response to suction applied at the proximal end of the tube. The proximal end 76 of tube 74 is disposed in a molded member having a frusto-conical forward section 78, a hollow intermediate section 77 and a rearward section comprising the drive tang 72. A bore extends transversely through the intermediate section 77 which is recessed to a reduced radial dimension at the bore openings 79. The proximal end 76 of the hollow cutting blade tube 74 communicates with this bore so that aspirated material received in tube 74 ca flow out of the cutting blade through bore openings 79. Drive tang 72 is received in a cup-like spring retainer member 80 that is open at both ends. Spring retainer member 80 has an annular lip projecting radially inward at its forward end and adapted to engage a radially outward projecting lip on the rearward section of the molded member from which drive tang 72 extends. The molded member, including sections 78, 77 and 72, and spring retainer 80 are preferably made of plastic so that the spring retainer can be forced into place on the molded member into a position whereby the two lips prevent mutual disengagement. A helical spring 81 is disposed inside spring retainer 80 to surround the drive tang 72 and serve to bias the rearward end of the spring retainer away from the blade. In this manner, spring 81 urges the two annular lips axially against one another in the absence of any axial force in opposition to the spring. Whereas tube 74 and burr 73 are made of metal (preferably stainless steel), the remainder of the inner member 71 is preferably made of plastic.

Outer member 70 includes a hollow metal (preferably stainless steel) tube 82 having an inside diameter which is larger than the outside diameter of tube 74 in inner member 71. The length of tube 82 is such that the distal end of tube 74, including the cutting blade 73 and opening 75, project through the open distal end of tube 82 when inner member 71 is inserted into and through inner member 70 in the manner described below. In this regard the inner and outer members are conventional. Tube 82 extends through a hollow hub preferably made of plastic material and having a short hollow frusto-conical forward end 83 formed integrally with a cylindrical section 84 having an annular rearward-facing surface that is ultrasonically welded or otherwise sealingly disposed against a fixed forward-facing annular surface 85 of a hollow cylindrical section 86. Immediately rearward of hollow section 86 is a hollow cylindrical section 87 of reduced outer diameter. A proximal end section 88 of the hub takes the form of a hollow cylinder with an outer diameter corresponding to that of sections 86 and 84. A central bore 89 extends longitudinally through the integrally formed molded plastic sections 86, 87 and 88 and is generally cylindrical except at its proximal end where it has a frusto-conical contour 90 to receive the frusto-conical section 78 of the inner member 71. Bore 89 is sized to permit tube 74 to extend therethrough, and through a similar aligned bore in sections 83 and 84, into tube 82. The cutting blade, when thusly assembled, has the forward-facing annular shoulder of section 77 of the inner member 71 disposed proximate the rearward-facing proximal end of rearward section 88 of outer member 70. The arrangement permits the inner member 70 to rotate within outer member 70 about the axis of tube 74.

As best illustrated in FIGS. 16 and 17, one or more cylindrical recesses 91 are defined in hub section 86 at the forward-facing surface 85. The number of such recesses 91 provided for any given cutting blade depends upon the optimal rotational speed range for that blade. Specifically, there are three possible speed ranges in the system of the preferred embodiment, although it will be apparent that any number of speed ranges may be designed into the system. For low speed blades, hub section 86 has no recesses defined in surface 85. For medium speed blades, hub section 86 has one recess 91 defined therein at a location radially spaced from the central bore 89 (as illustrated in FIG. 16). For high speed blades, hub 86 has two recesses 91 disposed symmetrically on opposite sides of the central bore 89 (as illustrated in FIGS. 17). Each recess 91 receives a magnet 92 that serves as a coding element for the blade. The material from which the hub is fabricated must be such as to permit the magnetic field of magnets 92 to be sensed in handpiece 11 when the cutting blade is inserted therein (in the manner described below). In order to assure proper orientation of magnet 92 in the handpiece, hub section 86 is formed with a locator stub 93 projecting a short distance radially outward from section 86 at a prescribed annular location on the hub circumference. Specifically, stub 93 is displaced 90° from each of the two possible angular orientations of recesses 91.

Referring again to FIGS. 3-8, locking ring 16 is provided with a central aperture 101 extending longitudinally therethrough and aligned with bore section 50 in body member 40. The diameters of aperture 101 and bore section 50 are slightly greater than the diameter of hub sections 86 and 88 and spring retainer 80. Locator stub 93 in hub sections 86, however, projects radially beyond the boundary of aperture 101 and bore section 50. In order to permit the cutting blade assembly to be accommodated into the handpiece through aperture 101, a radially-extending slot 102 is defined in locking ring 16 at the periphery of aperture 101. A corresponding radially-extending slot 103 is disposed at the periphery of bore section 50 and is sized to permit locator stub 93 to be received therein when the cutting blade assembly is inserted into the handpiece in the manner described below.

As best illustrated in FIG. 10, the forward-facing end surface 104 of body member 40 is provided with two generally cylindrically recesses 105, 106 disposed on diametrically opposite sides of bore section 50 and radially spaced from that bore section. Recesses 105 and 106 are spaced on opposite sides and 90° from slot 103, and each has a generally cylindrical reed switch assembly 107 disposed therein. Reed switch assembly 107, which is illustrated in greater detail in FIG. 11, includes a pair of normally open switch contacts 108, 109 embedded in a glass capsule 12 or potting compound, along with respective lead wires 110, 111 which are insulated and extend from the rearward end of the capsule. The reed switches are oriented to sense the presence of respective magnets 93 in the blade assembly hub so as to register the coded speed range information from the inserted blade. This information, in the form of open/closed conditions of contacts 108, 109, is transmitted to the control circuity in the console 10 via wires 110, 111. The insulated wires 110, 111 at the rear of the reed switch assembly pass into respective recesses 105, 106 and through respective obliquely oriented wire-conducting channels 113, 114. These channels terminate in a generally rectangular recessed space 115 in the top side of forward section 41, immediately below the switch cluster 17 and its associated printed circuit board 116. The rear wall of recess 115 opens to a channel 117 that runs rearwardly for the remaining length of body member 40. Channel 117 conducts reed switch wires 110, 111 and wires from printed circuit board 116 to the rearward end of body member 40 where the wires form part of cable 12 along with the wires connected to motor 51. The wires in cable 12 conduct signals to and from the circuitry in the control console.

A bore 118 extends from the forward end of surface 104 of body member 40 into recess 115. Bore 118 is used during assembly of the handpiece unit as an access opening for potting compound. Once sufficient potting compound has been delivered into the handpiece, bore 118 is sealed by a set screw 119 and additional compound.

Referring again to FIG. 6, an aspiration path for excised tissue material flowing through hollow tube 74 and out through bore openings 79 in the cutting blade is provided via widened bore section 47. Specifically, when the cutting blade assembly is properly inserted into the handpiece, section 77 of the molded part of the inner blade member 71 is disposed within bore section 44. Openings 79 are clear from the bore walls to permit aspirated material to flow into bore section 47 and through an oblique channel 120 extending both rearwardly and toward the top side of body member 40 until terminating in a suction channel 121. This suction channel extends rearwardly in parallel spaced relation to wire channel 117 until reaching the rearward end of body member 40 where it communicates, via end cap 13, with suction tube 14. As described above, the suction tube 14 communicates with a source of suction pressure (not shown) via a control valve (not shown) to permit selective aspiration from the surgical site. The O-ring 49 disposed in bore section 48 surrounds hub section 86 of the cutting blade assembly to provide a pressure seal forwardly of the aspiration chamber formed by bore section 44. Gasket 60 and O-rings 58, 59 provide pressure seals rearwardly of the aspiration chamber.

Locking ring 16 is a generally cylindrical member having an exposed forward-facing surface 130 and a rearward-facing surface 131 abutting surface 104 of body member 40. The locking ring is made of metal and includes a raised annular lip surrounding surface 131 and extending over a short length of the body member 40. A circular recess 132 in surface 130 is disposed concentrically about aperture 101. Arcuate channels 133, 134 are defined through the locking ring within recess 132. Channels 133 and 134 are equally spaced from slot 102 and are disposed symmetrically about aperture 101. Each channel subtends approximately 90° of arc at a constant radial distance from the center of aperture 101. A disc-shaped spacer 135 is disposed in recess 132 and is provided with a central aperture 140, aligned with aperture 101, and with two screw holes spaced by 180° and aligned with corresponding tapped bores in forward end surface 104 of body member 40. Screws 136, 137 pass through the screw holes and are threadedly engaged in the tapped bores to secure spacer 135 to body member 40. These screws pass through respective channels 134, 133 to permit locking ring 16 to be rotated relative to spacer 135 and body member 40. Such rotation is limited by the lengths of the channels 133, 134 (i.e., 90°). Spacer 135 also has a slot 138 defined therethrough to extend radially from central aperture 140. When slot 138 is rotatably aligned with slot 102 in locking ring 16, and with slot 103 in bore section 50, locator stub 93 on the cutting blade assembly can freely pass into and out of the body member 40.

The rearward-facing side of the locking ring 16, as seen in FIGS. 7 and 8, includes an arcuate ramp surface 141 extending approximately 140° from slot 102 along the outer edge of aperture 101 and the inner edge of arcuate slot 134. Ramp surface 141 serves as a camming surface for inserting the cutting blade into the handpiece. Specifically, in one extreme rotational position of locking ring 16, slot 102 is aligned with slot 138 in spacer 135 and with slot 103 in bore section 50. It is to be noted that slots 138 and 103 are permanently aligned but that slot 102 can be misaligned as a function of the rotation of the locking ring. When all the slots are aligned, the cutting blade assembly may be inserted through the locking ring as far as possible. The open rearward end of the spring retainer member slides over the forward end of the motor drive shaft 54 (as best illustrated in FIG. 6) until the edge of the opening in member 84 abuts the frusto-conical surface of the drive shaft immediately rearward of the forward end of the drive shaft. In this position the locator stub 93 on the cutting blade hub is disposed substantially entirely in slot 103 in bore section 50 with just a small portion of the stub projecting partially into slot 102 of the locking ring. If the locking ring is then rotated 90° to its other extreme position, the camming surface 141 gradually forces stub 93, and with it the cutting blade assembly, rearwardly. This pushes the drive tang 72, in opposition to the bias force of spring 81, further rearward in spring retainer 80 and into more positive engagement with the drive shaft 54. Thus, in the installed position of the blade assembly, spring 81 is axially compressed as camming surface 141 forces locator stub fully into the slot 103 in bore section 50.

In order to remove the cutting blade assembly, the locking ring is rotated 90° in the opposite direction to its initial extreme position, thereby gradually releasing the compression force on spring 81. When slot 102 becomes aligned with slots 138 and 103, spring 81 forces the cutting blade assembly slightly forward so that a portion of stub 93 extends into slot 102. The blade assembly may then be easily removed and replaced by another blade.

The two extreme positions of the locking ring are maintained by mean of a detent ball 143 and spring 144 located in a recess in forward-facing surface 104 of body member 40. The detent ball and spring cooperate with two dimples 145, 146 formed at 90° spaced locations in the rearward-facing surface of the locking ring to provide stops at the two extreme rotational positions of the locking ring. Dimples 145 and 146 are configured as spherical segments to match the configuration of ball 143. The locking ring 16 is retained in fixed axial or longitudinal position between the spacer 135 and body member 40 by means of screws 136, 137, but is free to rotate with respect to the spacer and body member by virtue of the 90° channels 133 and 134 that slide about the screws.

An important feature of the present invention is the switch cluster 17 located on the top side of body member 40 in forward section 41. Specifically, and referring to FIG. 6, a printed circuit board 116 is contoured to fit into a shallow recess in forward section 41 of body member 40. This shallow recess surrounds the deeper recess 115 so that lead wires from the printed circuit board can pass into the recess 115 and through wire conducting channel 117 to the cable assembly. The printed circuit board 116 is illustrated in greater detail in FIG. 14 and is transversely arcuate to match a segment of the circumference of forward section 41 of body member 40. Typically, the printed circuit board 116 is made from a rectangular blank or sheet of decarburized steel having a length (i.e., longitudinally of body member 40) of 0.998 inches, a width (i.e., along the circumference of forward section 41) of 1.294 inches and a thickness of 0.013 inches. The sheet is bent to be curved about its longitudinal center line with a radius of curvature of approximately 0.656 inches and so as to subtend an arc of 113°. It is to be understood that these dimensions are by way of example only are and not to be construed as limiting on the scope of the invention, except for the considerations set forth below. A layer of porcelain is deposited on each surface of the sheet, and the metal circuit elements are deposited, or otherwise formed, on the top porcelain surface. A pair of flaps 187, 188 at the center of the sheet are bent downwardly into recess 115 to provide access for lead wires running from the deposited circuitry on the top surface of the board to the handpiece cable via channel 117. The particular materials used in fabricating the printed circuit board 116 are important since the board must withstand autoclave temperatures without becoming brittle and breaking. This becomes a particularly important consideration where, as here, the printed circuit board must be curved at a relatively small radius of curvature. Typically, in order for the printed circuit board to conform to the curvature of the handpiece circumference, the radius of curvature is on the order of 0.6 to 0.7 inches, and usually is in the narrower range of 0.64 to 0.66 inches. Although the decarburized steel sheet with porcelain coatings on both sides is suitable for the printed circuit board of the present invention, I have found that other materials are also suitable. For example, the printed circuit board may be a sheet of aluminum on which a thick film process is employed to form a layer of epoxy with gold silk screening to define the circuit elements. Alternatively, the board may be a thin film TELFON (polytetrafluorethylene) weave board with copper laminate used to form the circuit elements. Another alternative is a fiberglass epoxy substrate with copper laminate forming the circuit elements.

Referring to FIGS. 12, 13, and 15, an integral electrically non-conductive silicone rubber sheet 150, having a Durometer on the order of seventy, is disposed atop the printed circuit board 116. A plurality of resilient push button switches 151, 152, 153 and 154 are defined in sheet 150. Each of pushbutton switches 151, 152 and 153 includes a resilient dome-like member 155 tapering from an open end facing the printed circuit board 116 to a closed end 156 remote from the printed circuit board. The closed end 156 encompasses a smaller area and has a smaller periphery than the open end. An electrically conductive member 157 is secured to the underside of the closed end 156. The electrically conductive member of each of pushbuttons 151, 152 and 153 is normally disposed in spaced alignment between a respective pair of contacts on the printed circuit board so that, when the pushbutton is depressed, those contacts are electrically bridged by the conductive member 157. Pushbutton switch 151 has a square-shaped closed end 156 and serves as the forward/reverse control switch. Pushbutton switches 152 and 153 are circular and serve as the decrease speed and increase speed control switches, respectively for the motor. Pushbutton switches 151, 152 and 153 are disposed in transversely aligned spaced relation along the circumference of the handpiece.

Pushbutton switch 154 is the on/off control switch for the motor and is generally oval-shaped. In this regard pushbutton switch 154 is slightly rearward of the aligned switches 151-153 and has a length along the circumference of the handpiece which corresponds approximately to the total spaced length of the aligned switches 151-153. In this manner the on/off switch 154 is immediately proximate any of the other three switches and can be quickly actuated to turn the motor on or off. Pushbutton switch 154 is also formed as a dome-like member 158 with a closed small end 159 and an open larger end. Three electrically conductive members 160, 161, 162 are secured in transversely spaced relation (i.e., in the same spaced relation as pushbutton switches 151, 152 and 153) to the underside of closed end 159 and are positioned opposite three respective pairs of contacts on the printed circuit board 116. These printed circuit board contacts are connected electrically parallel to one another so that bridging of any one or more of the contact pairs effects the same on/off function. In the preferred embodiment, electrically conductive member 160 is longitudinally aligned with electrically conductive member 157 of switch 151; electrically conductive member 161 is longitudinally aligned with electrically conductive member 157 of switch 152; and electrically conductive member 162 is longitudinally aligned with electrically conductive member 157 of switch 153. The transverse spacing of conductive members 160, 161 and 162 assure that substantially any location along the transverse dimension of switch 154 can be depressed to effect actuation of the on/off function. In this regard, the transverse spacing between successive electrically conductive members 160, 161 and 162 is only slightly greater than the transverse dimension of each of these individual electrically conductive members. For the given Durometer of sheet 150, effective actuation of switch 154 may be achieved from anywhere along the transverse dimension of that switch.

The circuitry on printed circuit board 116 is illustrated in FIG. 14 to which specific reference is now made. All contact pairs for all four switches 151, 152, 153 and 154 include one contact associated with a common lead 170 serving as a circuit ground in the system control circuitry. In this regard, lead 170 surrounds the other leads on three sides and includes six contacts 171, 172, 173, 174, 175 and 176 at spaced locations along its length. A second lead 177 is associated only with on/off switch 154 and includes three contacts 178, 179 and 180 along its length. Contacts 176 and 178 are closely spaced from one another and are positioned under electrically conductive member 162 to be electrically bridged by that member when it is pressed against the printed circuit board 116. In a similar manner contacts 175 and 179 are positioned to be selectively bridged by conductive member 161, and contacts 174 and 180 are positioned to be selectively bridged by electrically conductive member 160.

A third lead 181 has a single contact 182 positioned adjacent but spaced from ground contact 173 so that these two contacts can be selectively bridged by the electrically conductive member 157 of the forward/reverse switch 151. A fourth lead 183 has a single contact 184 positioned adjacent but spaced from ground contact 172 so that these two contacts can be selectively bridged by the electrically conductive member 157 of the decrease speed switch 152. A fifth lead 185 has a single contact 186 positioned adjacent but spaced from ground contact 171 so that these two contacts can be selectively bridged by the electrically conductive member 157 of the increase speed switch 153.

All five leads 170, 177, 181, 183 and 185 extend along one or the other of the centrally located and downwardly bent flaps 187, 188 to connect to appropriate wires in recess 115. As noted above, such wires are conducted through channel 117 to the cable assembly at the rearward end of the handpiece.

A metal cover plate or bezel 190 is disposed over sheet 150 and is apertured to permit pushbuttons 151, 152, 153 and 154 to project therethrough. A plurality of screw holes disposed about the border of plate 190 are aligned with respective holes in sheet 150 and with edge notches in printed circuit board 116 in order to secure these elements together and to body member 40 via respective screws threadedly engaging respective tapped bores in the shallow body member recess in which printed circuit board 116 resides.

All of the components of the handpiece 11 are made of materials that are capable of withstanding the high temperatures to which they are exposed when the handpiece is sterilized by autoclaving or the like. A potting compound or epoxy is used to protect the electrical components from damage during autoclaving.

With brief reference to FIG. 9, the forward section 84 of the hub member for the cutting blade may be colored in a manner to match the border of one of the indicators 26, 27, 28 so as to provide a color-coded indication on the cutting blade of the speed range corresponding to the correspondingly color coded indicator border.

The body member 40 is made of lightweight material and is balanced to facilitate small joint arthroscopy. Longitudinally-extending fluting along the length of the body member facilitates handling. The body member houses a powerful brushless motor providing the necessary torque and speed for all types of powered arthroscopic procedures. The location of switch cluster 17 on the handpiece greatly facilitates operation by the surgeon. Automatic speed range is provided without the need for heavy adapters which must be sterilized after each surgical procedure. Although the motor may be completely controlled from the handpiece, a footswitch is provided to permit control over forward and reverse rotation while allowing the surgeon to select the proper speed from the handpiece. The entire handpiece and cord may be immersed and soaked in a sterilized solution without corroding. In addition, the unit may be flashed, steamed autoclaved or gas sterilized.

The use of disposable, single-use cutting blades assures factory-fresh sharpness with every surgical procedure and eliminates the expense and time delay involved in sharpening and re-sharpening blades.

Operation is controlled by a sophisticated microprocessor system. The microprocessor and related electronic circuitry, of itself, does not constitute part of the present invention; however, for purposes of fully disclosing the best mode of carrying out the invention, a microprocessor and related electronic circuitry are disclosed herein in FIGS. 18 through 23 and are briefly described in the following paragraphs. It is to be understood, however, that the microprocessor and electronic system described herein serve as only one embodiment for effecting the inventive features described above, and that other arrangements of electronic circuits and/or microprocessor units may be used to effect the inventive features. In furtherance of the requirement for disclosing the best mode of carrying out the invention, the application includes appendices containing a program listing for the microprocessor and a list of the components illustrated in the circuits of FIGS. 18–23.

Figure 19:
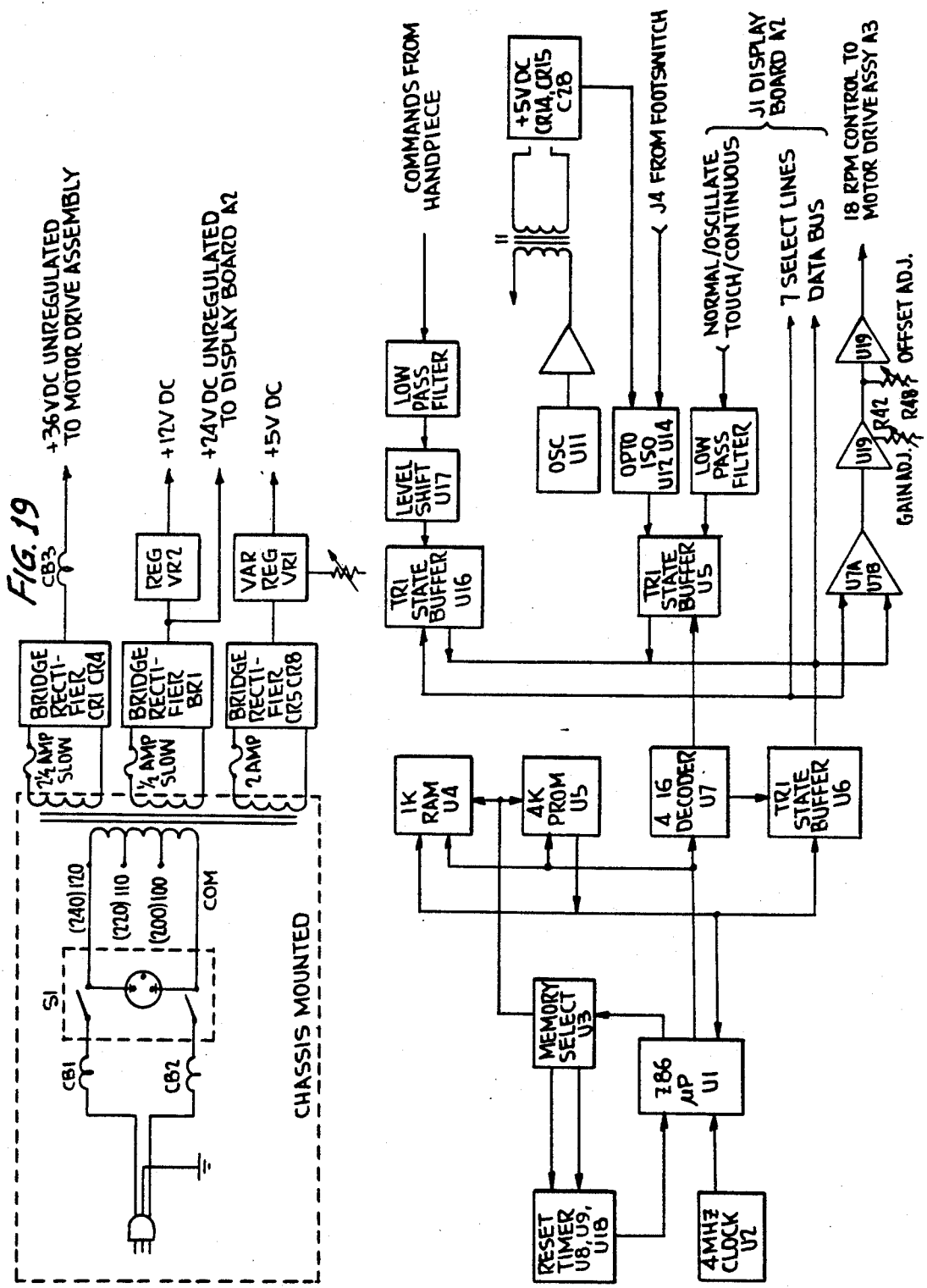
FIG. 19 is a functional block diagram of the control board.
Figure 20:
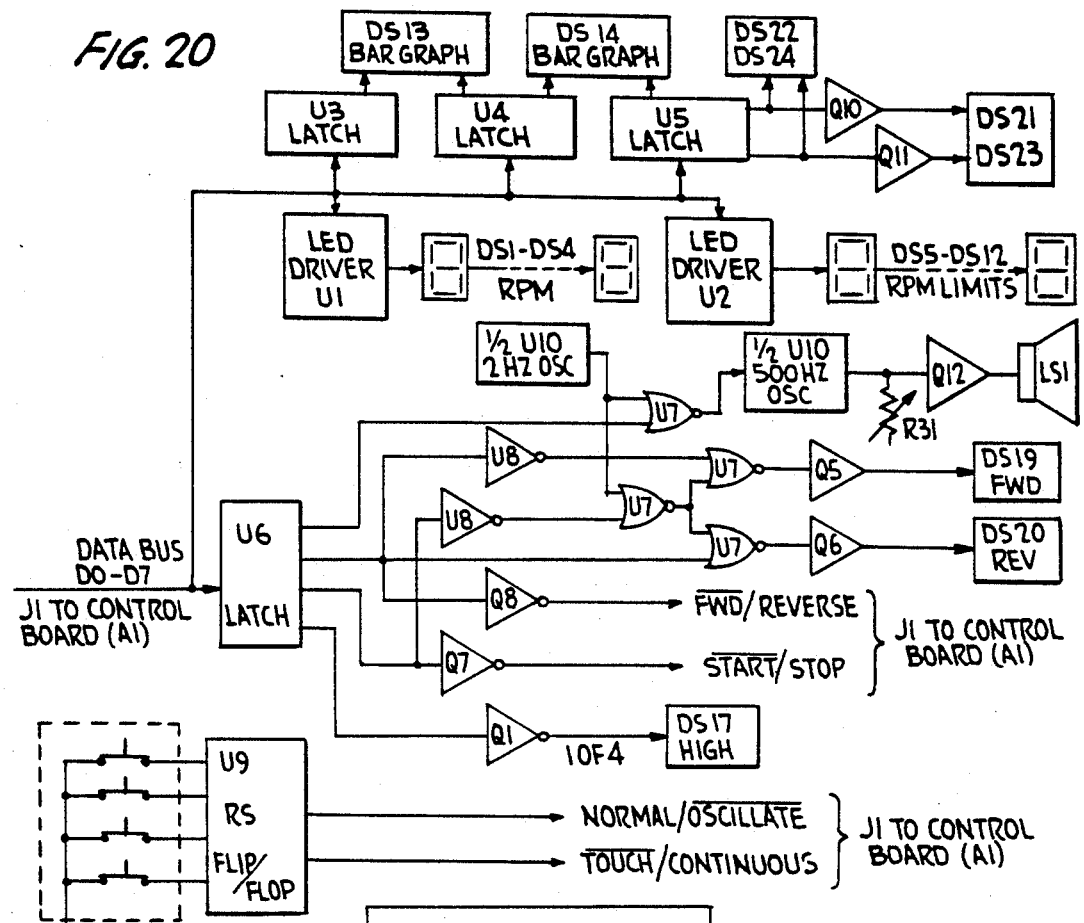
FIG. 20 is a functional block diagram of the display board located in the control console.
Figure 22:
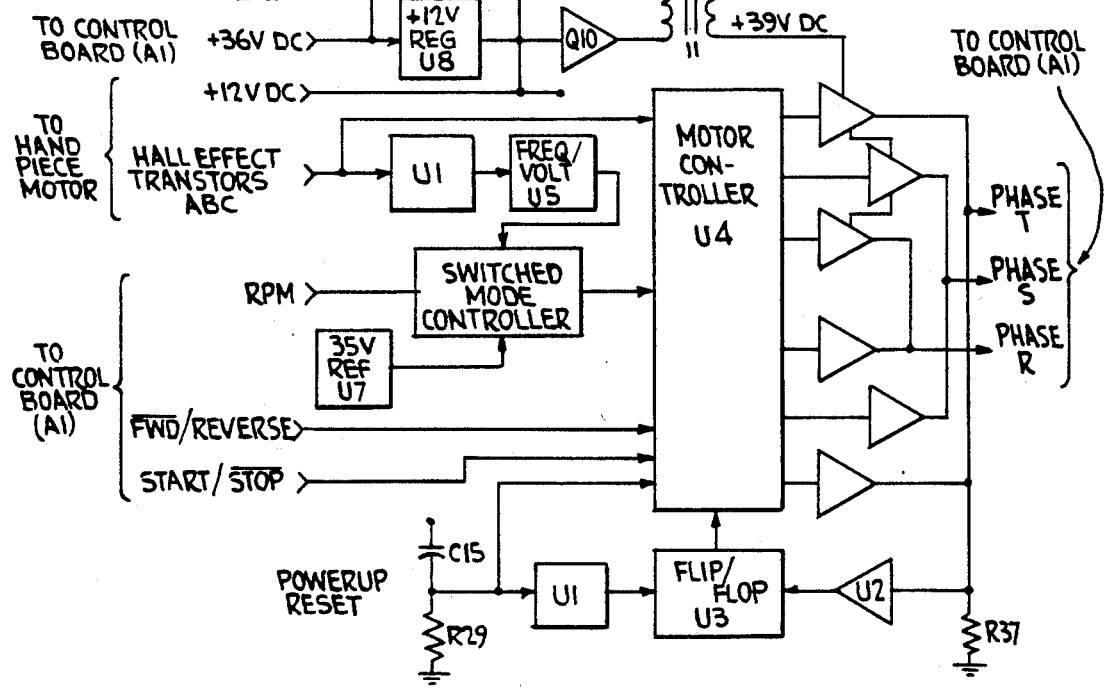
FIG. 22 is a functional block diagram of the motor drive assembly located in the control console.
Figure 21A:
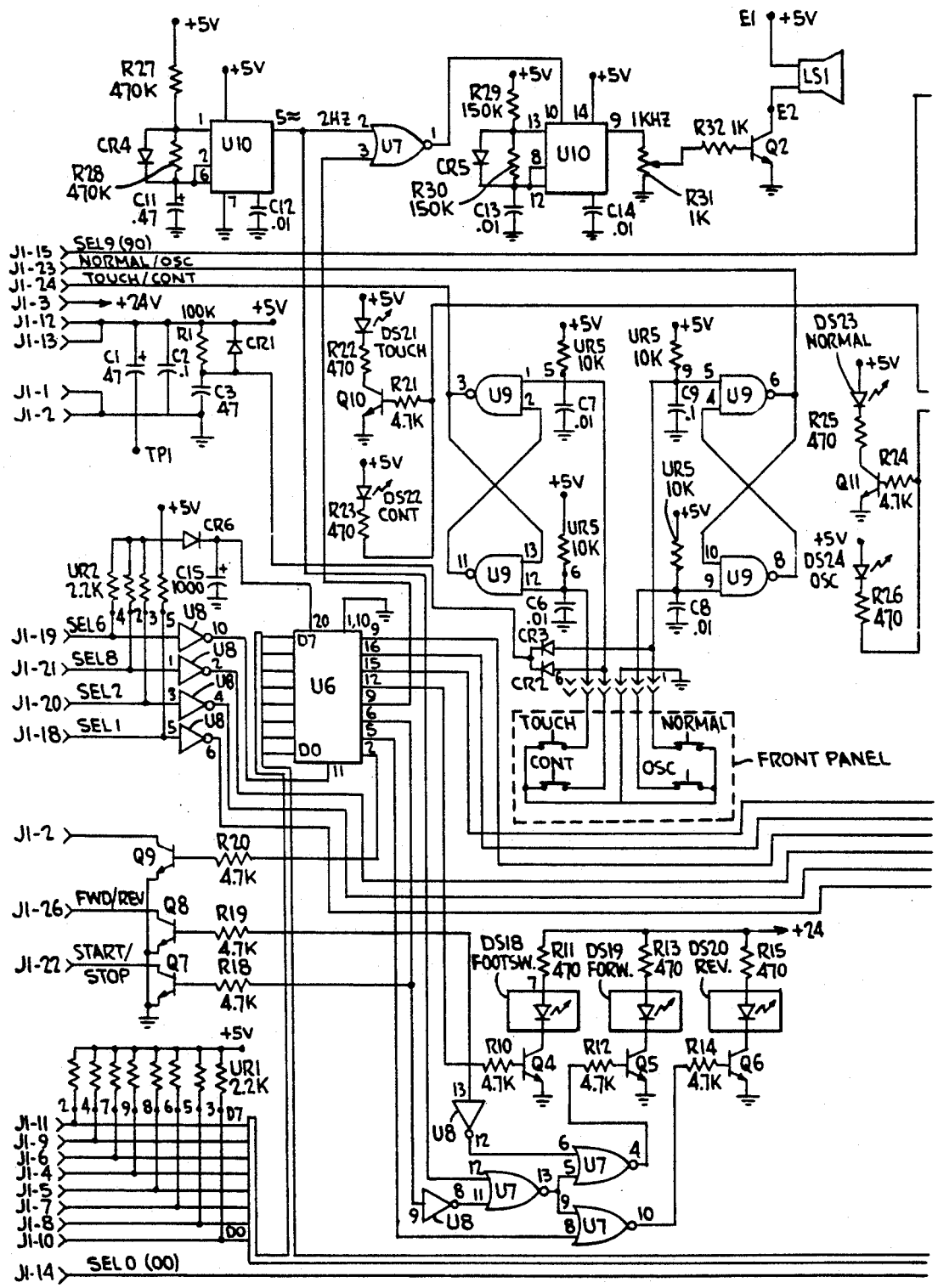
FIG. 21 is a detailed schematic diagram of the display board.
Figure 21B:
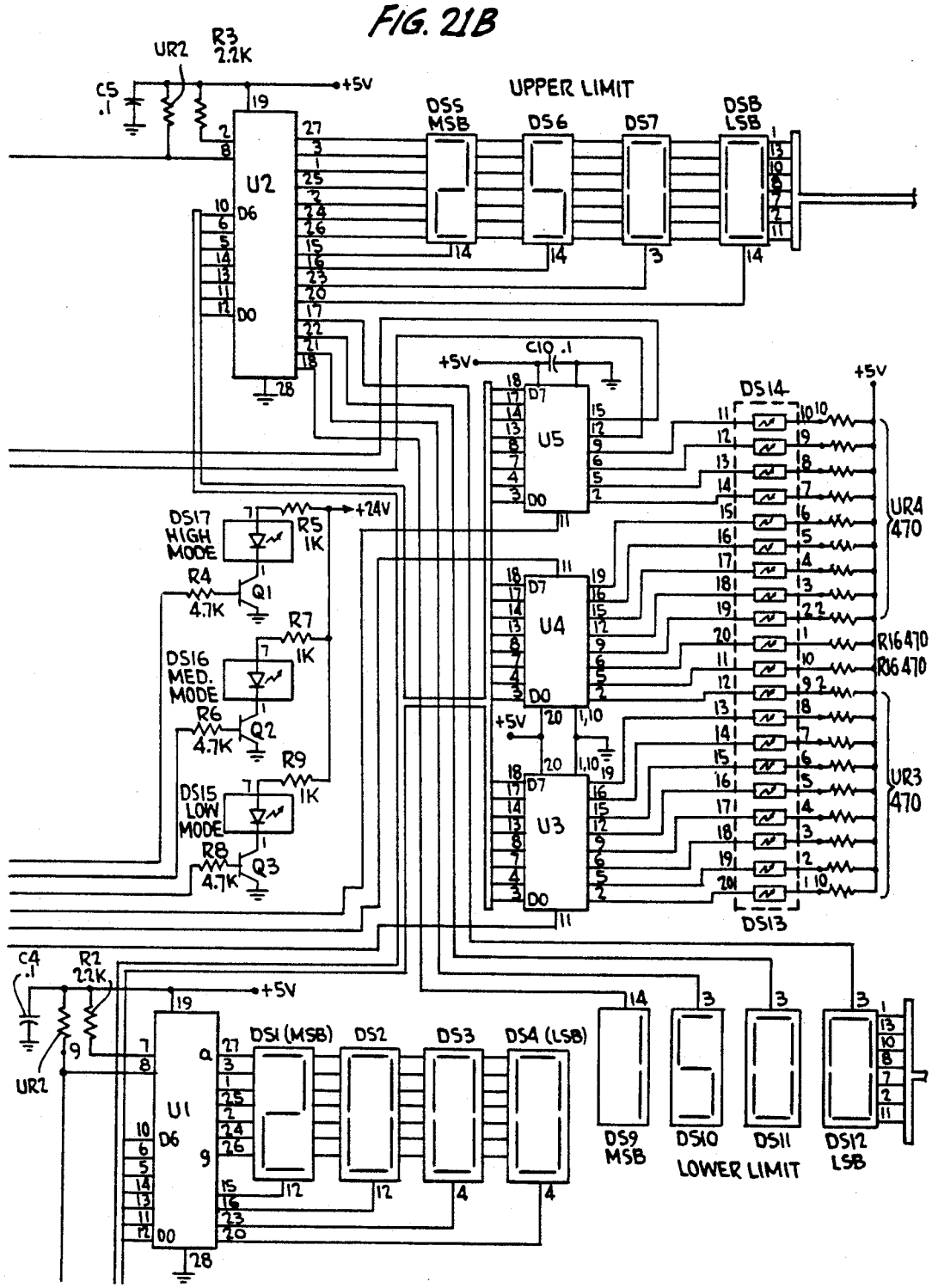
Figure 23B:
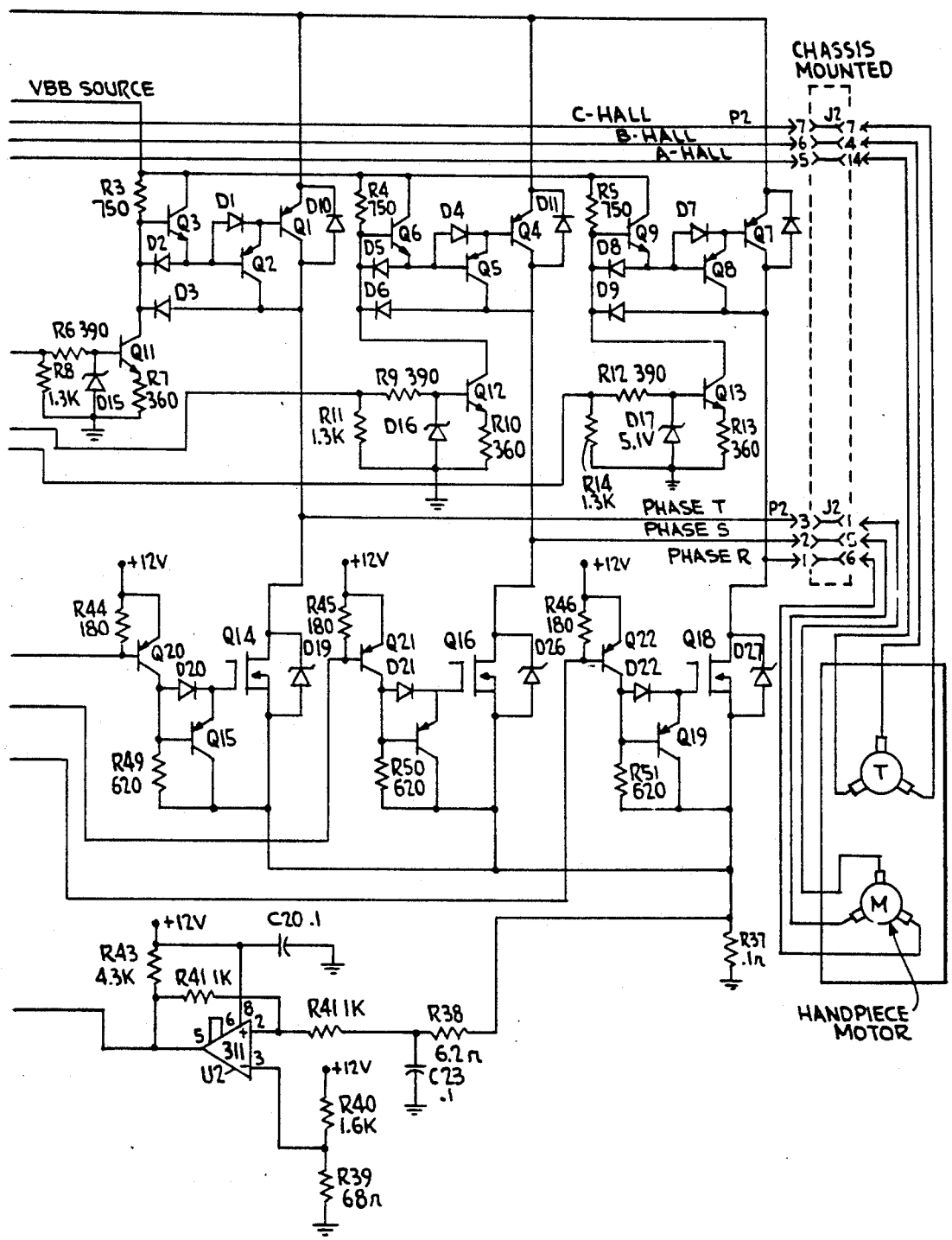
FIG. 23 is a detailed schematic diagram of the motor drive assembly.

The electronic components are provided on three circuit boards, namely the control board illustrated in FIGS. 18 and 19, the display board illustrated in FIGS. 20 and 21, and the motor drive assembly illustrated in FIGS. 22 and 23. The circuitry present on each of these circuit boards is described below. Referring first to the electrical schematic diagram in FIG. 18 and the functional block diagram in FIG. 19 for the control board, it will be seen that the control board includes four sections, namely, the power supplies, the microprocessor, the signal input section, and the digital-to-analog output section. The power supply section furnishes two regulated d.c. voltages of +5 volts and +12 volts for internal circuit requirements. It also provides an unregulated d.c. +36 volts for the handpiece drive unit. The system is internally wired for a nominal 115 volts 50/60 Hz operation. Mains transformer T1 has a multiple-tap primary winding for 100, 110 and 120 volt operation, or 200, 220 and 240 volt operation. The mains power is supplied to transformer T1 via jack J1, circuit breakers CB1 (and CB2 for 230 volts a.c. units) and mains power switch S1. Transformer T1 includes three secondary windings for providing 9.2 volts, 18 volts and 28 volts. The 28 volts a.c. winding is fused by a fuse F1, rectified by bridge CR1–CR4 and filtered by capacitor C1. The unregulated +36 volts d.c. is used to drive motor 51 in the handpiece. The 18 volts a.c. winding is fused by fuse F3 and rectified by bridge BR1. Capacitor C5 serves to filter this voltage which is regulated to +12 volts d.c. by voltage regulator VR2. The 9.2 volts a.c. winding is fused by fuse F2 and rectified by bridge rectifier CR5–CR8. The rectified voltage is filtered by capacitor C2 and regulated to +5 volts d.c. via voltage regulator VR1.

The CPU section contains a Z-80 type microprocessor with 1 Kbyte of random access memory, 4 Kbytes of EPROM memory, a reset circuit, clock, address decoders and the line driver/buffer circuit. The Z-80 microprocessor U1 is clocked at 4 MHz by a quartz crystal controlled oscillator U2.

The program monitor reset circuit in the CPU section includes a dual timer U10, NAND gates U8, U9, and transistors Q1, Q2. These components provide the power "on" reset and cause a system restart if the processor jumps to an illegal address or becomes caught in a programming loop. Switch S1 may be utilized for trouble shooting purposes when in the "inhibit" position, reset pulses are disconnected from the CPU integrated circuit U1. The system may be manually started by momentarily grounding pin 26 of CPU U1 to determine whether or not there is a problem with the program monitor unit.

Two sections of integrated circuit U8 form a cross-coupled RS flip-flop. The flip-flop is toggled each time the correct sequence of addressing is initiated by the program. The flip-flop pulses ar utilized to trigger the second section of the timer U10. If the program fails to toggle the flip-flop (indicating improper program execution), capacitor C11 charges to a threshold level and triggers the timer to begin a reset pulse from the power supply section.

Transistor Q2 provides the discharge path for capacitor C11. Transistor Q1 assures full discharge of capacitor C11 by feeding back the discharge pulse to the base of transistor Q2 The time constant established by resistor R16 and capacitor C11 sets the minimum time allowed between address pulses from the program before a reset occurs. The time constant established by resistor R18 and capacitor C14 sets the reset pulse low time, and the time constant established by resistor R17 and capacitor C13 sets the "wait for initialize" time high after the restart.

Integrated circuit U4 is a 1 Kbyte random access memory utilized for stack operations and scratch pad memory purposes. Integrated circuit U5 is a 4 Kbyte EPROM in which the system program is stored. Integrated circuit U3 is a three-two-eight line decoder utilized for memory selection. Integrated circuit U7 is a four-two-sixteen line decoder providing input/output (I/O) selection for the system. The data buss is buffered from peripheral circuitry by integrated circuit U6.

The signal input section of the control board accepts commands from the handpiece, the footswitch, and from the front panel display board. Handpiece commands are RC-filtered, level-shifted by integrated circuit U17 from +12 volts to +5 volts d.c. and transferred onto the data buss via buffer U16. The RC-filtered front panel commands and the footswitch commands are transferred onto the data buss via buffer U15. The footswitch is electrically isolated from the system by optoisolators U12, U13 and U14.

The primary winding of transformer T1 is driven by transistor Q3 which is switched at a 25 KHz rate by oscillator U11. The secondary winding of transformer T1 is rectified and filtered to produce an isolated +5 volts d.c. that is then applied to the footswitch. When the footswitch is connected, it energizes optoisolator U13. When the footswitch "reverse" pedal is depressed, it energizes optoisolator U12. The forward pedal energizes optoisolator U14. The output signals from optoisolators U12, U13 and U14 are transferred onto the data buss by buffer U15.

The digital-to-analog section of the control board receives a digital word from the CPU U1 and converts it to an analog voltage that sets the motor speed via the drive assembly circuit (FIGS. 22, 23). The digital-to-analog convertor U18 converts the digital word to an analog voltage. This voltage is divided by resistors R38 and R40 and then RC-coupled to operational amplifier U19. Potentiometer R42 is used to set the maximum speed of 2500 rpm. The signal is then coupled to the offset amplifier where resistor R48 sets the minimum speed of 75 rpm. Thereafter the signal is routed to the drive assembly (FIGS. 22, 23) where it is used to set the motor speed.

The display board is illustrated in FIGS. 20 (functional block diagram) and 21 (detailed schematic). The display board controls the LED digit displays, the range bar graph and all of the indicator lamps at the console front panel. Commands are provided from the display board to the drive assembly (FIGS. 22, 23), and input signals are received by the display board from the front panel switches.

Each of the LED driver integrated circuits (U1 for actual speed display 32; U2 for upper and lower limit displays 29 and 31) contain an eight-by-four bit random access memory (RAM). Data to be displayed is written as a four-bit word. The low order four bits (D0-D3) contain the number to be written, and the high order four bits (D4-D7) contain the address to the internal RAM location. Each of the four-bit words are multiplexed to the seven-segment LED's at a two kilohertz rate by a clock that is internal to the driver integrated circuit.

Output latches U3, U4 and U5 receive digital information from the CPU to drive the bar graphs DS13, DS14 and LED's DS21-DS24.

Output latch U6 receives digital information from the CPU and controls the audio, the front panel indicators DS15-DS20, and output commands to the drive assembly (FIGS. 22, 23) via the control board (FIGS. 18, 19). Transistors Q7 and Q8 are employed to level shift the voltage from +5 to +12 volts d.c.

Audio speaker LS1 is driven by transistor Q12, the latter being switched at a 500 Hz rate by one-half of oscillator U10. Potentiometer R31 is utilized to internally set the audio sound level. The other half of oscillator U10 is a two Hz oscillator used to switch the 500 Hz audio oscillator to beep the audio and to blink the forward and reverse indicators when the motor is running.

Two sections of integrated circuit U9 form a cross-coupled RS flip-flop which accepts input signals from the touch switch 23 and the continuous switch 22 located at the front panel. Flip-flop U9 also provides an output signal to the control board (FIGS. 18, 19). The other two sections of the flip-flop U9 accept input signals from the "OSC" switch 24 and the "NORM" switch 25 located at the front panel.

The motor drive assembly board is illustrated in functional block diagram form in FIG. 22 and in a detailed schematic diagram in FIG. 23. The motor drive assembly is a closed loop three-phase system used to control the brushless d.c. motor 51 located in the handpiece 11.

Voltage regulator U8 develops +12 volts d.c. for internal circuit requirements and is also employed by the motor position sensors. Transistor Q10, transformer T1 and associated 4 components are employed to develop a voltage which is +3 volts d.c. higher than the voltage present at pin 2 of plug P1. This higher voltage is employed to turn off transistors Q1, Q4 and Q7. In addition, a −3.5 volts d.c. reference voltage is generated by voltage convertor U7 so as to be utilized by the switched mode controller U6.

There are three Hall effect transistors (A,B,C) located in motor 51 and serve to relay the motor position information to the motor controller U4. This information, along with the speed data information supplied by the switched-mode controller U6, is employed to provide electronic commutations of the motor windings. The three phases R, S and T are driven by the bipolar and field effect transistor switching output stages Q1-Q9 and Q11-Q22.

Over current circuitry is provided to protect the windings, the associated drivers, and the power supply. Voltage comparator U2 senses the voltage across resistor R37. If this voltage exceeds the preset limit, +12 volts is applied to motor controller U4 (at pin 12) via flip-flop U13 to disable the output signals. One-quarter of exclusive OR gate U1 is employed during the power-up state to supply a ground reference to the motor controller U4 (at pin 12) via flip-flop U13 for normal operation.

The Hall effect transistor signals from the motor are also used for velocity feedback in the closed loop system. These signals are combined and waved-shaped by exclusive OR gate U1 and applied to the frequency-to-voltage convertor U5. This d.c. voltage is then sent to the switched mode controller U6 which compares the voltage at pin 6 (rpm commanded from the control board) with the voltage at pin 15 (actual motor speed). This signal difference is then applied to the motor controller U4 to maintain a constant speed.

It is to be understood that the various specific dimensions presented by way of example herein are intended to be only exemplary unless otherwise stated.

From the foregoing description it will be appreciated that the invention makes available a novel drive system for an arthroscopic surgical instrument wherein the drive motor may be entirely controlled from the handpiece and wherein automatic speed range control is effected by directly coding the cutting blade assembly and thereby eliminating the need for an intermediate adapter. The unique arcuate printed circuit board, serving as part of the handpiece control switch cluster, permits that cluster to be contoured to fit generally within the contour of the handpiece so that the handpiece itself may be more easily manipulated and so that the individual switches in the switch cluster may be quickly and accurately accessed.

Having described a preferred embodiment of a new and improved electrosurgical instrument constructed in accordance with the present invention, it is believed that other modifications, variations and changes will be suggested to those skilled in the art in view of the techniques set forth herein. It is therefore to be understood that all such variations, modifications and changes are believed to fall within the scope of the present invention as defined in the appended claims.

APPENDIX I

This appendix contains a list of parts, with component values, employed in the electronic circuitry present in the control console 10. The list of components is divided into three sections representing the three circuit boards, respectively, described herein.

| Description | Reference Designator |
|---|---|
| Control Board Assy. | A1 |
| Capacitor .001 mfd 200V | C10,16 |
| Capacitor .01 mfd 100V | C12,15,17,19,21,22,23 |
| Capacitor .1 mfd 50V | C4,7-9,11,13,14,18,24-38 |
| Capacitor 10 mfd 50V | C20 |
| Capacitor 470 mfd 35V | C6 |
| Capacitor 1000 mfd 35V | C3, 5 |
| Capacitor 4700 mfd 25V | C2 |
| Capacitor 4700 mfd 50V | C1 |
| Rectifier, Bridge 2Amp | BR1 |
| Diode 3amp 200V | CR1-8 |
| Diode 1N4001 | CR11-19 |
| Suppressor 5V | CR9 |
| Suppressor 12V | CR10 |
| L.E.D. red | DS1-3 |
| Fuse 2.5 amp Slow | F1 |
| Fuse 2 amp Slow | F2 |
| Fuse 1/2 amp Slow | F3 |
| Clips, Fuse | XF1, F2, F3 |
| I.C. C.P.U. MK 3880N-4 | U1 |
| I.C. OSC. M1259-4M | U2 |
| I.C. 3-8 decoder 74LS138 | U3 |
| I.C. RAM MK4801AN-3 | U4 |
| I.C. EPROM 2732A Oper. Prog. | U5 |
| I.C. Buffer 74LS245 | U6, 15, 16 |
| I.C. 4-16 decoder 74LS154 | U7 |
| I.C. Nand gate 74LS132 | U8, 9 |
| I.C. Timer 556 | U10 |
| I.C. Timer 555 | U11 |
| I.C. Optoisolator 4N38A | U12, 13, 14 |
| I.C. Inverter 4049 | U17 |
| I.C. D/A converter AD558JN | U18 |
| I.C. Op Amp LM358 | U19 |
| I.C. Nand gate 4093 | U20 |
| I.C. Inverter 74HC4049 | U21 |
| Resistor 39, 5% 1/2w | R23 |
| Resistor 47, 5% 1/4w | R24-26 |
| Resistor 100, 5% 1/4w | R14,24-26 |
| Resistor 120, 5% 1/4w | R4 |
| Resistor 220, 5% 1/2w | R22 |
| Resistor 270, 5% 1/4w | R3 |

| Description | Reference Designator |
|---|---|
| Resistor 1K, 5% 1/4w | R5,7,8,11,15,30,31 |
| Resistor 2.2K, 5% 1/4w | R6, 9 |
| Resistor 4.7K, 5% 1/4w | R13,27-29,38,40 |
| Resistor 6.8K, 5% 1/4w | R1, 19 |
| Resistor 10K, 5% 1/4w | R10,12,21,32-37,39,49-52 |
| Resistor 22K, 5% 1/4w | R20 |
| Resistor 68K, 5% 1/4w | R43 |
| Resistor 100K, 5% 1/4w | R41, 44-47 |
| Resistor 220K, 5% 1/4w | R17, 18 |
| Resistor 1M, 5% 1/4w | R16, 53 |
| Resistor Network 2.2K | UR1-3 |
| Resistor Network 10K | UR4 |
| Potentiometer 200 | R2 |
| Potentiometer 1K | R48 |
| Potentiometer 50K | R42 |
| Regulator, Adj. LM350K, +5V | VR1 |
| Regulator, LM340T12, +12V | VR2 |
| Switch SPDT Slide | S1 |
| Transistor, PN2222A NPN | Q1, 2, 4 |
| Transistor, 2N3019 NPN | Q3 |
| Transformer, Isolation | T1 |
| Plug Housing 2 position | A3P1 |
| Plug Housing 4 position | A3P3 |
| Contact, Leaf | X A3P1, A3P3 |
| Header, 4 pin | J4 |
| Header, 7 pin | J2 |
| Header, 26 pin Rt. Ang. | J1 |
| Receptacle, 6 pin | J3 |
| Key, Header polarization | XJ1 |
| Heatsink TO-3 | XVR1 |
| Heatsink TO-5 | XQ3 |
| Heatsink TO-220 | XVR2 |
| Mount, 14 Pin Dip | XU2 |
| Terminal, Turret | E1-8, TP1-7 |
| Mount, TO5 | XQ3 |
| Display Board Assy | A2 |
| Cable Assembly - 26 Pin | J1 |
| Capacitor .01mfd 100V | C6-9, 12-14 |
| Capacitor .1mfd 50V | C2, 4-5, 10 |
| Capacitor .47mfd 35V | C3, C11 |
| Capacitor 47mfd 25V | C1 |
| Diode 1N4001 | CR1, 4, 5 |
| Diode 1N277 | CR2, 3 |
| Display, 7 segment (.8") HDSP-3900 | DS1-4 |
| Display, 7 segment (.3") 5082-7730 | DS5-12 |
| LED, Red bar graph, HDSP-4820 | DS13, 14 |
| LED, Red light bar HLMP-2685 | DS15-17 |
| LED, Yel light bar HLMP-2785 | DS18 |
| LED, Grn light bar HLMP-2885 | DS19, 20 |
| LED, Red | DS21-24 |
| I.C. LED driver, ICM 7218CIJI | U1, 2 |
| I.C. Latch, 74LS373 | U3-5 |
| I.C. Latch, 74HC373 | U6 |

| Description | Reference Designator |
|---|---|
| I.C. Norgate, 74LS02 | U7 |
| I.C. Inverter, 74LS04 | U8 |
| I.C. Nandgate, 74HC132 | U9 |
| I.C. Timer, 556 | U10 |
| Transistor PN2222A NPN | Q1-12 |
| Resistor, 470, 5% 1/4w | R11,13,15,16,17, 22,23,25,26 |
| Resistor, 1K, 5% 1/4w | R5,7,9,32 |
| Resistor, 2.2K, 5% 1/4w | R2, 3 |
| Resistor, 4.7K, 5% 1/4w | R4, 6, 8, 10, 12, 14, 18-21, 24 |
| Resistor, 100K, 5% 1/4w | R1 |
| Resistor, 150K, 5% 1/4w | R29, 30 |
| Resistor, 470K 5% 1/4w | R27, 28 |
| Resistor, network 470 | UR3,4 |
| Resistor, network 2.2K | UR1,2 |
| Resistor, network 10K | UR5 |
| Potentiometer, 1K | R31 |
| Header, 6Pin | J2 |
| Mount, 16 Pin .3 | XDS13-20 |
| Speaker 8ohm | LS1 |
| Capacitor 680 pfd Ceramic | C15 |
| Capacitor .0015mfd Ceramic | C19 |
| Capacitor .01mfd Ceramic | C5,612 |
| Capacitor .022mfd Ceramic | C3 |
| Capacitor .1mfd Ceramic | C1,4,7,8,11,13 14,16,17,20,23 |
| Capacitor .22mfd Ceramic | C18 |
| Capacitor 1.5mfd 6V Tantalum | C9 |
| Capacitor 6.8mfd 6V Tantalum | C2 |
| Capacitor 100mfd 16V Electrolytic | C21,22 |
| Capacitor 330mfd 50V Electrolytic | C10 |
| Diode IN4148 | D1-9,14,18,20,21 22,25 |
| Diode IN4001 50V 1 amp | D23 |
| Diode MUR805 50V 8 amp | D10-12 |
| Diode IN5225 3V Zener .5w | D13 |
| Diode IN4732B 4.7V Zener .5w | D24 |
| Diode IN5231 5.1V Zener .5w | D15-17 |
| Diode IN4754A 39VZener 1w | D19,26,27 |
| I.C. EX-OR Gate 4070 | U1 |
| I.C. Volt. Comparator LM311 | U2 |
| I.C. Flip-Flop 4013 | U3 |
| I.C. Motor controller S7261 | U4 |
| I.C. V/Freq. converter LM331 | U5 |
| I.C. Sw-mode controller UC3637 | U6 |
| I.C. Volt. converter ICL7660CPA | U7 |
| I.C. Volt. Regulator LM317T | U8 |
| Resistor 0.1 5% 2w | R37 |
| Resistor 6.2 5% 1/4w | R38 |

| Description | Reference Designator |
|---|---|
| Resistor 9.1 5% 1/4w | R2 |
| Resistor 68 5% 1/4w | R39 |
| Resistor 180 5% 1/4w | R44-46 |
| Resistor 220 5% 1/4w | R47 |
| Resistor 240 5% 1/4w | R36 |
| Resistor 360 5% 1/4w | R7,10,13 |
| Resistor 390 5% 1/4w | R6,9,12 |
| Resistor 620 5% 1/4w | R49-51 |
| Resistor 750 5% 1/4w | R3-5 |
| Resistor 1K 5% 1/4w | R41 |
| Resistor 1.2K 5% 1/4w | R1 |
| Resistor 1.3K 5% 1/4w | R8,11,14 |
| Resistor 1.6K 5% 1/4w | R40 |
| Resistor 2.1K 5% 1/4w | R35 |
| Resistor 3.3K 5% 1/4w | R31,32 |
| Resistor 4.3K 5% ;/4w | R43 |
| Resistor 4.7K 5% 1/4w | R26-28,30,34 |
| Resistor 6.81K 1% 1/4w | R16 |
| Resistor 10K 5% 1/4w | R17,18,20 |
| Resistor 15K 5% 1/4w | R21,48 |
| Resistor 30K 5% 1/4w | R29 |
| Resistor 51K 5% 1/4w | R25 |
| Resistor 68K 5% 1/4w | R19,33 |
| Resistor 100K 5% 1/4w | R15 |
| Resistor 160K 5% 1/4W | R42 |
| Resistor 300K 5% 1/4w | R24 |
| Resistor 510K 5% 1/4w | R22 |
| Potentiometer 10K | R23 |
| Transistor D45H5 PNP | Q1,4,7 |
| Transistor ZTX750 PNP | Q2,5,8,15,17,19 |
| Transistor 2N3904 NPN | Q3,6,9 |
| Transistor ZTX 650 NPN | Q10-13 |
| Transistor BUZ 71A N-CHANNEL | Q14,16,18 |
| Transistor 2N3906 PNP | Q20-22 |
| Transformer, Toroid | T1 |
| Connector, 2 pin | P1 |
| Connector, 4 pin | P3 |
| Connector, 8 pin | P2 |

APPENDIX II

This appendix contains a program listing for software employed in the microprocessor in an embodiment of the invention that has actually been constructed and tested. The program listing contains both object code and source code and was employed on a Z80 microprocessor.

```
LOCATION OBJECT CODE LINE#    SOURCE LINE

1               "Z80"    LIST
                         2   ; CONCEPT, INC. - FRED REXROTH MAR 14, 1986
                         3   * DWG. NO. 145-132 REV C
                         4   *
                         5   *
    (0000)               6   REVIEW    EQU    0         ;PROG REVIEW
    (0070)               7   BBB       DEFL   60H
    (0050)               8   BBBB      DEFL   50H
    (0010)               9   BAA1      DEFL   10H
    (0020)              10   BAA2      DEFL   20H
    (0060)              11   BAA3      DEFL   60H
    (0020)              12   DAC       DEFL   20H
    (0040)              13   FEW       DEFL   40H
    (0050)              14   HEW       DEFL   50H
    (0060)              15   LITE      DEFL   60H
                        16   ***
                        17             EXT    FLOT
                        18             EXT    FIXX
                        19             EXT    FMOV
                        20             ORG    0220H
0000 DD2142FF           21             LD     IX,42FFH   ;SP POS
0004 DCFS               22             LD     SP,IX
0006 F3                 23             DI                ;NO INTERRUPT
0007 210001             24             LD     HL,0001H
000A 224017             25             LD     (CTR53),HL
000D 3E00               26             LD     A,00
000F 22401E             27             LD     (CTR43),A
0012 3E00               28             LD     A,00H
0014 324200             29             LD     (INBUF3),A
0017 324000             30             LD     (FLAG63),A
001A D320                31            OUT    (DAC2),A
001C CD077B             32            CALL    CHECK     ;LIGHTS TEST
001F C2004C             33            JP      MOTOR
0022 DB47               34 IDLE       IN      A,(FEW3)
0024 CB47               35            BIT     0,A       ;FEW ON ?
0026 2800F               36            JR      NZ,NOFEW  ;JP IF NO
0028 3A4000             37            LD      A,(INBUF3)
002B CBF7               38            SET     6,A
002D 324200             39            LD      (INBUF3,A
0030 3A4200             40            LD      A,(OUTBUF3)
0032 CBE7               41            SET     4,A       ;FEW LITE ON
0035 1800               42            JR      JP1
0037 3A4000             43 NOFEW      LD      A,(INBUF3)
003A CBB7               44            RES     6,A
003C 324200             45            LD      (INBUF3,A
003F 3A4200             46            LD      A,(OUTBUF3)
0042 CBA7               47            RES     4,A       ;FEW LITE OFF
```

```
LOCATION OBJECT CODE LINE      SOURCE LINE 0044  324003      48  JP1      LD    (OUTBUF),A
0047  D3E0        49           OUT   (LITES),A
0049  AF          50           XOR   A              ;ZERO A REG
004A  32421D      51           LD    (OLDINBO),A
004D  D3A0        52           OUT   (DACO),A       ;NIN ROM
004F  3A4002      53           LD    A,(OUTBUF)
0052  CB57        54           RES   2,A            ;ACTIVATE ETOR
0054  324003      55           LD    (OUTBUF),A
0057  D3E0        56           OUT   (LITES),A      ;ETOR
0059  220200      57  OPER     LD    (000040),A
005C  220000      58           LD    (000040),A
005F  DB40        59           IN    A,(FEH)
0061  CB6F        60           BIT   5,A            ;MOT OR TRIP
0063  2847        61           JR    Z,MOTOR        ;NO,JP
0065  0E00        62           LD    C,BEB
0067  3A400F      63           LD    A,(FLAGS)
006A  CB67        64           BIT   4,A            ;DEPLY TO ZERO ?
006C  2812        65           JR    Z,SET2         ;YES,JP
006E  3E00        66           LD    A,00H
0070  ED79        67           OUT   (C3),A
0072  3E10        68           LD    A,10H
0074  ED79        69           OUT   (C3),A
0076  3E20        70           LD    A,20H
0078  ED79        71           OUT   (C3),A
007A  3E30        72           LD    A,30H
007C  ED79        73           OUT   (C3),A
007E  1810        74           JR    CKCTR
0080  3E0F        75  SET2     LD    A,0FH
0082  ED79        76           OUT   (C3),A
0084  3E1F        77           LD    A,1FH
0086  ED79        78           OUT   (C3),A
0088  3E2F        79           LD    A,2FH
008A  ED79        80           OUT   (C3),A
008C  3E2F        81           LD    A,2FH
008E  ED79        82           OUT   (C3),A
0090  2A4017      83  CKCTR    LD    HL,(CTRS)
0093  2B          84           DEC   HL
0094  224017      85           LD    (CTRS),HL
0097  7C          86           LD    A,H
0098  B5          87           OR    L
0099  20B7        88           JR    NZ,IDLE
009B  3A400F      89  RLOAD    LD    A,(FLAGS)
009E  EE10        90           XOR   10H
00A0  32400F      91           LD    (FLAGS),A
00A3  21DFFF      92           LD    HL,0FFFH
00A6  224017      93           LD    (CTRS),HL
00A9  C20022      94           JP    IDLE
00AC  CD00DA      95  MOTOR    CALL  RANGE          ;GET SPEED RANGE
00AF  CD21E0      96           CALL  SPDX           ;SPEED CHANGE
00B2  CD231D      97           CALL  MODE           ;MOTOR DIR
00B5  CD24D0      98           CALL  INDCD          ;DECIMAL SPEED
00B8  CD0523      99           CALL  DISP           ;DIGITS/LITES
00BB  FD210300   100           LD    IY,00200H
00BF  CD0662     101           CALL  WAIT
00C2  3A4002     102           LD    A,(INBUF)
00C5  CB67      103            BIT   4,A            ;? RUN MOTOR
00C7  CA0022    104            JP    Z,IDLE
00CA  CD0665    105            CALL  RUN
00CD  C20059    106            JP    OPER
                 107
                 108 *** SUBROUTINE TO SET SPEED RANGE ***
```

```
LOCATION OBJECT CODE LINE      SOURCE LINE

00D2 214000      109 RANGE    LD    HL,INBUF
  00D5 7E          110          LD    A,(HL)
  00D6 CB7F        111          BIT   7,A           ;FULL SPD RNG ?
  00D8 C0          112          RET   NZ            ;RET IF YES
  00D9 DD214001    113          LD    IX,BPLR
  00DD DBE0        114          IN    A,(HEH0)
  00DF E603        115          AND   03H           ;MASK
  00E1 47          116          LD    B,A
  00E2 7E          117          LD    A,(HL)
  00E3 E603        118          AND   03H           ;CP OLD CODE
  00E5 B8          119          CP    B
  00E6 C8          120          RET   Z
  00E7 78          121          LD    A,B
  00E8 FE00        122          CP    00H           ;?EHAVER
  00EA 2013        123          JR    NZ,REBCT
  00EC 110B91      124          LD    DE,LORNG      ;SET HI LO LIM
  00EF CD015C      125          CALL  DIGITE
  00F2 1100EB      126 FALT     LD    DE,225D
  00F5 DD7300      127          LD    (IX+00),E
  00F8 DD7201      128          LD    (IX+01),D
  00FB 3E0D        129          LD    A,0DH
  00FD 77          130          LD    (HL),A
  00FE C9          131          RET
  00FF FE02        132 REBCT    CP    02H           ;?REBECTOR
  0101 201E        133          JR    NZ,EURR
  0103 110699      134          LD    DE,MIDRNG     ;SET HI LO LIM
  0106 CD015C      135          CALL  DIGITE
  0109 1102BC      136          LD    DE,0700D
  010C DD7300      137          LD    (IX+00),E
  010F DD7201      138          LD    (IX+01),D
  0112 3E0E        139          LD    A,0EH
  0114 77          140          LD    (HL),A
  0115 CD0131      141          CALL  FWDBIT
  0118 C9          142          RET
  0119 FE01        143 EURR     CP    01H           ;?EURR
  011B 2005        144          JR    NZ,FALT
  011D 110BA1      145          LD    DE,HIRNG      ;SET HI LO LIM
  0120 CD015C      146          CALL  DIGITE
  0123 1107D0      147          LD    DE,2000D
  0126 DD7300      148          LD    (IX+00),E
  0129 DD7201      149          LD    (IX+01),D
  012C 3E0D        150          LD    A,0DH
  012E 77          151          LD    (HL),A
  012F CD0131      152          CALL  FWDBIT
  0132 C9          153          RET
                   154 *
  0133 3A4000      155 FWDBIT   LD    A,(INBUF3)
  0136 CBD7        156          SET   2,A           ;SET MOT FWD
  0138 324000      157          LD    (INBUF3),A
  013B 2101EA      158          LD    HL,OUTF
  013E 18B9        159          JR    CHMOT
  0140 3A4000      160 REVBIT   LD    A,(INBUF3)
  0143 CB97        161          RES   2,A           ;SET MOT REV
  0145 324000      162          LD    (INBUF3),A
  0148 2101E4      163          LD    HL,OUTR
  014B 3A4003      164 CHMOT    LD    A,(OUTBUF3)
  014E CB57        165          BIT   2,A           ;MOT ON ?
  0150 C0          166          RET   NZ            ;RET IF YES
  0151 E9          167          JP    (HL)
  0152 CBCF        168 OUTF     SET   1,A
  0154 18AE        169          JR    OUTE
```

```
LOCATION OBJECT CODE LINE          SOURCE LINE

0154 CBEF          170 OUTR        RES     5,A
0156 324002        171 OLITE       LD      (OUTBUF3),A
0159 D350          172             OUT     (LITE3),A
015B C9            173             RET
                   174 *
                   175 *** SUBROUTINE TO DRIVE 7 SEGMENT DISPLAYS ***
015C 0E50          176 DIGITS      LD      C,BEEH
015E 0604          177             LD      B,004H
0160 210000        178             LD      HL,0BH
0163 CD0560        179 NXTDIG      CALL    DIGIT
0166 2D            180             DEC     L
0167 20FA          181             JR      NZ,NXTDIG
0169 214000        182             LD      HL,INBUF
016C C9            183             RET
                   184 *** SUBROUTINE TO CHANGE SPEED ***
016D DD214001      185 SPDX        LD      IX,SPLB
0171 D350          186             IN      A,(HEW)
0173 47            187             LD      B,A
0174 CBEF          188             BIT     5,A          ;SPEED UP
0176 CA0265        189             JP      Z,SPDN       ;NO, JP
0179 DDEE00        190             LD      L,(IX+00)
017C DDEE01        191             LD      H,(IX+01)
017F 3A4000        192             LD      A,(INBUF3)   ;TEST RANGE
0182 E603          193             AND     03H
0184 FE00          194             CP      00H          ;LO RANGE ?
0186 2053          195             JR      NZ,MIDR      ;NO, JUMP
0188 110300        196             LD      DE,0400D
018B ED52          197             SBC     HL,DE
018D 2028          198             JR      NZ,SPDUP     ;NO, JP
018F CD0210        199             CALL    AUDOFF
0192 3A4000        200             LD      A,(INBUF3)
0195 CB7F          201             BIT     7,A          ;FULL SPD RNG ACTV ?
0197 C0            202             RET     NZ           ;YES, JP
0198 FD21FFFF      203             LD      IY,0FFFFH
019C CD0652        204             CALL    WAIT
019F CD0652        205             CALL    WAIT
01A2 CD0652        206             CALL    WAIT
01A5 D350          207             IN      A,(HEW)
01A7 CBEF          208             BIT     5,A          ;SPX UP SW ACTV ?
01A9 C8            209             RET     Z            ;NO, RET
01AA 214000        210             LD      HL,INBUF
01AD DD214001      211             LD      IX,SPLB
01B1 110BA5        212             LD      DE,FULANG
01B4 CD0350        213             CALL    DIGITS
01B7 110420        214             LD      DE,1250D
01BA DD7200        215             LD      (IX+00),E
01BD DD7301        216             LD      (IX+01),D
01C0 3E0C          217             LD      A,0CH
01C2 77            218             LD      (HL),A
01C3 CD0353        219             CALL    FWDBIT       ;SET FWD DIR
01C6 C9            220             RET
01C7 DDEE00        221 SPDUP       LD      L,(IX+00)
01CA DDEE01        222             LD      H,(IX+01)
01CD 23            223             INC     HL
01CE DD7500        224             LD      (IX+00),L
01D1 DD7401        225             LD      (IX+01),H
01D4 3A4000        226             LD      A,(INBUF3)
01D7 CBAF          227             RES     5,A          ;CANCEL JOB
01D9 224000        228             LD      (INBUF3),A
01DC CD0265        229             CALL    AUDON
```

| LOCATION | OBJECT CODE | LINE | | SOURCE LINE | | |
|---|---|---|---|---|---|---|
| 01DF | CD02F0 | 220 | | CALL | SPEED | |
| 01E2 | C9 | 221 | | RET | | |
| 01E3 | FE02 | 222 | MIDR | CP | 02H | |
| 01E5 | 201C | 223 | | JR | NZ,HIR | |
| 01E7 | 110284 | 224 | | LD | DE,05000 | ;HI LIMIT |
| 01EA | ED52 | 225 | | SBC | HL,DE | |
| 01EC | F20310 | 226 | | JP | P,AUDOFF | |
| 01EF | DD6E00 | 227 | | LD | L,IIX+03 | |
| 01F2 | DD6601 | 228 | | LD | H,IIX+13 | |
| 01F5 | 23 | 229 | | INC | HL | |
| 01F6 | DD7500 | 240 | | LD | IIX+03,L | |
| 01F9 | DD7401 | 241 | | LD | IIX+13,H | |
| 01FC | CD0205 | 242 | | CALL | AUDON | |
| 01FF | CD02F0 | 243 | | CALL | SPEED | ;DELAY |
| 0202 | C9 | 244 | | RET | | |
| 0203 | 1109C4 | 245 | HIR | LD | DE,25000 | |
| 0206 | 37 | 246 | | SCF | | |
| 0207 | 3F | 247 | | CCF | | |
| 0208 | ED52 | 248 | | SBC | HL,DE | |
| 020A | 2020 | 249 | | JR | NZ,RPMUP | |
| 020C | CD0310 | 250 | | CALL | AUDOFF | |
| 020F | 2A4000 | 251 | | LD | A,IINBUF3 | |
| 0212 | CB7F | 252 | | BIT | 7,A | ;FULL SPD RNG ? |
| 0214 | C8 | 253 | | RET | Z | ;RET IF NO |
| 0215 | DB50 | 254 | | IN | A,(HEW) | |
| 0217 | CB6F | 255 | | BIT | 5,A | ;RPM UP ACTV ? |
| 0219 | C8 | 256 | | RET | Z | ;RET IF NO |
| 021A | FD21FFFF | 257 | | LD | IY,0FFFFH | |
| 021E | CD0652 | 258 | | CALL | WAIT | |
| 0221 | CD0652 | 259 | | CALL | WAIT | |
| 0224 | CD0652 | 260 | | CALL | WAIT | |
| 0227 | DB50 | 261 | | IN | A,(HEW) | |
| 0229 | CB6F | 262 | | BIT | 5,A | ;RPM UP ACTV ? |
| 022B | C8 | 263 | | RET | Z | ;RET IF NO |
| 022C | 214000 | 264 | | LD | HL,INBUF | |
| 022F | DD214001 | 265 | | LD | IX,SPLB | |
| 0233 | 110691 | 266 | | LD | DE,LOANS | |
| 0236 | CD0350 | 267 | | CALL | DIGITS | |
| 0239 | 1100E8 | 268 | | LD | DE,2250 | |
| 023C | DD7200 | 269 | | LD | IIX+03,E | |
| 023F | DD7201 | 270 | | LD | IIX+13,D | |
| 0242 | 3E0C | 271 | | LD | A,0CH | |
| 0244 | 77 | 272 | | LD | (HL),A | |
| 0245 | CD0131 | 273 | | CALL | FWDBIT | |
| 0248 | C9 | 274 | | RET | | |
| 0249 | DD6E00 | 275 | RPMUP | LD | L,IIX+03 | |
| 024C | DD6601 | 276 | | LD | H,IIX+13 | |
| 024F | 23 | 277 | | INC | HL | |
| 0250 | DD7500 | 278 | | LD | IIX+03,L | |
| 0253 | DD7401 | 279 | | LD | IIX+13,H | |
| 0256 | 2A4000 | 280 | | LD | A,IINBUF3 | ;CANCEL JOG |
| 0259 | CBAF | 281 | | RES | 5,A | |
| 025B | 324000 | 282 | | LD | IINBUF3,A | |
| 025E | CD0205 | 283 | | CALL | AUDON | |
| 0261 | CD02F0 | 284 | | CALL | SPEED | |
| 0264 | C9 | 285 | | RET | | |
| 0265 | CB67 | 286 | SPDN | BIT | 4,A | ;SP DOWN? |
| 0267 | CA0310 | 287 | | JP | Z,AUDOFF | ;NO JP |
| 026A | DD5E00 | 288 | | LD | E,IIX+03 | |
| 026D | DD5601 | 289 | | LD | D,IIX+13 | |
| 0270 | 2A4000 | 290 | | LD | A,IINBUF3 | |

```
LOCATION OBJECT CODE LINE        SOURCE LINE

0273  E623           291                AND   02H
0275  FE01           292                CP    01H       ;HI RNG ?
0277  2018           293                JR    NZ,MRIM   ;NO,JP
0279  21DC05         294                LD    HL,1500D
027C  37             295                SCF
027D  3F             296                CCF
027E  ED52           297                SBC   HL,DE
0280  CA0210         298                JP    Z,AUDOFF
0283  1B             299                DEC   DE
0284  DD7300         300                LD    [IX+00],E
0287  DD7301         301                LD    [IX+01],D
028A  CD0205         302                CALL  AUDON
028D  CD02F0         303                CALL  SPEED
0290  C9             304                RET
0291  FE02           305 MRIM           CP    02H       ;MED RNG ?
0293  2018           306                JR    NZ,LRIM   ;NO,JP
0295  2101F4         307                LD    HL,0500D  ;LD LIMIT
0298  37             308                SCF
0299  3F             309                CCF
029A  ED52           310                SBC   HL,DE     ;SPD - LD SPD LIMIT ?
029C  CA0210         311                JP    Z,AUDOFF  ;JP IF YES
029F  1B             312                DEC   DE
02A0  DD7300         313                LD    [IX+00],E
02A3  DD7301         314                LD    [IX+01],D
02A6  CD0205         315                CALL  AUDON
02A9  CD02F0         316                CALL  SPEED
02AC  C9             317                RET
02AD  3A4000         318 LRIM           LD    A,[INBUF3]
02B0  CBEF           319                BIT   5,A       ;JOG ACTV ?
02B2  C0             320                RET   NZ        ;YES JP
02B3  210043         321                LD    HL,075D   ;LD LIMIT
02B6  37             322                SCF
02B7  3F             323                CCF
02B8  ED52           324                SBC   HL,DE     ;DE HAS OLD SPEED
02BA  CA02CB         325                JP    Z,AEP
02BD  1B             326                DEC   DE
02BE  DD7300         327                LD    [IX+00],E
02C1  DD7301         328                LD    [IX+01],D
02C4  CD0205         329                CALL  AUDON
02C7  CD02F0         330                CALL  SPEED
02CA  C9             331                RET
02CB  CD0210         332 AEP            CALL  AUDOFF
02CE  FD21FF00       333                LD    IY,0FF00H
02D2  CD0E52         334                CALL  WAIT
02D5  DB50           335                IN    A,[IN3]
02D7  CB67           336                BIT   4,A       ;? SPEED ON
02D9  C8             337                RET   Z         ;NO JP
02DA  3A4000         338                LD    A,[INBUF3]
02DD  CBEF           339                SET   5,A       ;JOG
02DF  324000         340                LD    [INBUF3],A
02E2  3A400E         341                LD    A,[GRAPH+2]
02E5  CBEF           342                SET   5,A       ;TOUCH LITE ON
02E7  32400E         343                LD    [GRAPH+2],A
02EA  D320           344                OUT   [BAR2],A
02ED  CD0321         345                CALL  FWDBIT
02EF  C9             346                RET
                     347 *
02F0  FD21FFFF       348 SPEED          LD    IY,0FFFFH
02F4  3A401E         349                LD    A,[CTR+3]
02F7  FE00           350                CP    00H
02F9  F202FD         351                JP    P,SLD
```

```
LOCATION OBJECT CODE LINE       SOURCE LINE

02FC C9              252            RET                      ;FAST SPD EXIT
 02FD 3D              253   SLO      DEC    A
 02FE 324036          254            LD     [CTR4],A
 0301 CD2E52          255            CALL   WAIT              ;SLOW SPD EXIT
 0304 C9              256            RET
                      257   *
 0305 3A4003          258   AUDON    LD     A,[OUTBUF3]
 0308 CB9F            259            RES    3,A
 030A 324003          260   AUDIO    LD     [OUTBUF3],A
 030D D3E0            261            OUT    [LITE],A
 030F C9              262            RET
                      263   *
 0310 3E08            264   AUDOFF   LD     A,08D
 0312 324036          265            LD     [CTR4],A
 0315 3A4003          266            LD     A,[OUTBUF3]
 0318 CBDF            267            SET    3,A
 031A 18EE            268            JR     AUDIO
                      269   *
                      270   *** SUBROUTINE TO SET MOTOR DIRECTION ***
 031C D850            271   MODE     IN     A,[SW1]
 031E 5F              272            LD     E,A
 031F CB47            273            BIT    0,A               ;HI SPD SW ?
 0321 202F            274            JR     NZ,FAR            ;YES, JP
 0323 DB40            275            IN     A,[SW]
 0325 CB5F            276            BIT    3,A               ;DEC ?
 0327 2020            277            JR     NZ,FAR            ;NO, JP
 0329 2A4001          278            LD     HL,[SPD]
 032C 01D205          279            LD     BC,05D2
 032F 37              280            SCF
 0330 3F              281            CCF
 0331 ED42            282            SBC    HL,BC             ;SPD > 500 ?
 0333 F20362          283            JP     P,FAR             ;YES, JP
 0336 3A4000          284   SETDEC   LD     A,[INBUF3]
 0339 CB9F            285            RES    3,A               ;SET DEC MODE
 033B 324000          286            LD     [INBUF3],A
 033E 3A400E          287            LD     A,[GRAPH+23]
 0341 CBA7            288            RES    4,A
 0343 32400E          289            LD     [GRAPH+23],A
 0346 D380            290            OUT    [BAR2],A
 0348 187E            291            JR     JOB
 034A FE01            292   FDRU     CP     01H               ;HI RNG
 034C 2014            293            JR     NZ,FAR            ;NO, JP
 034E 3A4000          294            LD     A,[INBUF3]
 0351 CBDF            295            SET    3,A               ;CONT
 0353 324000          296            LD     [INBUF3],A
 0356 3A400E          297            LD     A,[GRAPH+23]
 0359 CBE7            298            SET    4,A               ;SET NORM MODE
 035B 32400E          299            LD     [GRAPH+23],A
 035E D380            400            OUT    [BAR2],A
 0360 1812            401            JR     FROMR
 0362 3A4000          402   FAR      LD     A,[INBUF3]
 0365 CBDF            403            SET    3,A               ;SET CONT MODE
 0367 324000          404            LD     [INBUF3],A
 036A 3A400E          405            LD     A,[GRAPH+23]
 036D CBE7            406            SET    4,A               ;SET NORM MODE
 036F 32400E          407            LD     [GRAPH+23],A
 0372 D380            408            OUT    [BAR2],A
 0374 3A4000          409   FROMR    LD     A,[INBUF3]
 0377 CB6F            410            BIT    5,A               ;JOB ACTV ?
 0379 204D            411            JR     NZ,JOB            ;YES, JP
 037B DB40            412            IN     A,[SW]
```

| LOCATION | OBJECT CODE | LINE | | SOURCE LINE | | |
|---|---|---|---|---|---|---|
| 027D | CB47 | 413 | | BIT | 0,A | ;FFW IN ? |
| 027F | 2835 | 414 | | JR | Z,FIN | ;YES,JP |
| 0281 | 3A4000 | 415 | | LD | A,[INBUF] | |
| 0284 | CB87 | 416 | | RES | 0,A | ;RES FFW FLG |
| 0286 | 324000 | 417 | | LD | [INBUF],A | |
| 0289 | 3A400F | 418 | | LD | A,[FLAGS] | |
| 028C | CB4F | 419 | | BIT | 1,A | ;F/R FLG ACTV ? |
| 028E | C20474 | 420 | | JP | NZ,SW2ACT | ;YES JP |
| 0291 | CB53 | 421 | | BIT | 2,E | ;F/R SW ACTV ? |
| 0293 | 2822 | 422 | | JR | Z,JOG | ;NO,JP |
| 0295 | CBCF | 423 | | SET | 1,A | ;SET F/R DEB FLG |
| 0297 | 32400F | 424 | | LD | [FLAGS],A | ;SAVE FLAGS |
| 029A | 21001F | 425 | | LD | HL,01FH | ;SET DEB COUNTER |
| 029D | 224012 | 426 | | LD | [CTR2],HL | |
| 02A0 | 3A4000 | 427 | | LD | A,[INBUF] | |
| 02A3 | EE04 | 428 | | XOR | 04H | ;TOGGLE BIT 2 |
| 02A5 | 324000 | 429 | | LD | [INBUF],A | |
| 02A8 | CB57 | 430 | | BIT | 2,A | ;FWD/REV ? |
| 02AA | 2805 | 431 | | JR | Z,REV | ;JP IF REV |
| 02AC | CD0321 | 432 | | CALL | FWDBIT | ;SET FWD |
| 02AF | 1817 | 433 | | JR | JOG | |
| 02B1 | CD032E | 434 REV | | CALL | REVBIT | ;SET REV |
| 02B4 | 1812 | 435 | | JR | JOG | |
| 02B6 | 3A4000 | 436 FIN | | LD | A,[INBUF] | |
| 02B9 | CBF7 | 437 | | SET | 6,A | ;FFW FLG |
| 02BB | 324000 | 438 | | LD | [INBUF],A | |
| 02BE | 3A400E | 439 | | LD | A,[GRAPH+2] | |
| 02C1 | CBEF | 440 | | SET | 5,A | ;TOUCH MODE |
| 02C3 | 32400E | 441 | | LD | [GRAPH+2],A | |
| 02C6 | D380 | 442 | | OUT | [BAR2],A | |
| 02C8 | 3A4000 | 443 JOG | | LD | A,[INBUF] | |
| 02CB | CBEF | 444 | | BIT | 5,A | ;? JOG MODE |
| 02CD | 2813 | 445 | | JR | Z,NOJOG | ;JP IF NO |
| 02CF | AF | 446 | | XOR | A | |
| 02D0 | 32400F | 447 | | LD | [FLAGS],A | |
| 02D3 | CD0321 | 448 | | CALL | FWDBIT | |
| 02D6 | 3A400E | 449 | | LD | A,[GRAPH+2] | ;SET CONT LITE |
| 02D9 | CBE7 | 450 | | SET | 4,A | |
| 02DB | 32400E | 451 | | LD | [GRAPH+2],A | |
| 02DE | D380 | 452 | | OUT | [BAR2],A | |
| 02E0 | 1810 | 453 | | JR | JOGBIT | |
| 02E2 | DB40 | 454 NOJOG | | IN | A,[FWD] | |
| 02E4 | CBE7 | 455 | | BIT | 4,A | ;TOUCH OR CONT ? |
| 02E6 | 2020 | 456 | | JR | NZ,ACONT | ;JP IF CONT |
| 02E8 | 3A400E | 457 | | LD | A,[GRAPH+2] | |
| 02EB | CBEF | 458 | | SET | 5,A | |
| 02ED | 32400E | 459 | | LD | [GRAPH+2],A | |
| 02F0 | D380 | 460 | | OUT | [BAR2],A | |
| 02F2 | 3A4000 | 461 JOGBIT | | LD | A,[INBUF] | |
| 02F5 | CB77 | 462 | | BIT | 6,A | ;FFW PLUGED IN? |
| 02F7 | 200D | 463 | | JR | NZ,CKFFW | ;JP IF YES |
| 02F9 | CB5B | 464 | | BIT | 3,E | ;FFW ON/OFF ACTV ? |
| 02FB | 2809 | 465 | | JR | Z,CKFFW | ;NO,JP |
| 02FD | 3A4000 | 466 | | LD | A,[INBUF] | |
| 0400 | CBE7 | 467 | | SET | 4,A | ;RUN MOT |
| 0402 | 324000 | 468 | | LD | [INBUF],A | |
| 0405 | C9 | 469 | | RET | | |
| 0406 | 3A4000 | 470 CKFFW | | LD | A,[INBUF] | |
| 0409 | CB77 | 471 | | BIT | 6,A | ;FFW IN ? |
| 040B | C2040C | 472 | | JP | NZ,FONF | ;YES,JP |
| 040E | CBA7 | 473 | | RES | 4,A | ;STOP MOT |

```
LOCATION OBJECT CODE LINE      SOURCE LINE
0410  324000      474           LD    [INBUF],A
0413  C9          475           RET
0414  214005      476  ADOF     LD    HL,FLAG5
0417  3A400E      477           LD    A,[GRAPH+2]
041A  CBAF        478           RES   5,A
041C  324005      479           LD    [GRAPH+2],A
041F  D320        480           OUT   [BAR2],A
0421  CB46        481           BIT   0,[HL]        ;ON/OFF FLAG ACTIVE?
0423  202B        482           JR    NZ,EW1ACT     ;YES, JP
0425  3A4000      483           LD    A,[INBUF]
0428  CB77        484           BIT   6,A           ;F/W ACTIV ?
042A  200A        485           JR    NZ,CWFEW      ;YES, JP
042C  CB5B        486           BIT   3,E           ;? ON/OFF ACTIVATED
042E  2005        487           JR    NZ,EWON       ;YES, JP
0430  CB5E        488           BIT   3,[HL]        ;NOT ON IN CONT MODE?
0432  2802        489           JR    Z,CWFEW       ;NO, JP
0434  C9          490           RET
0435  CBCE        491  EWON     SET   1,[HL]        ;SET ON/OFF DES ACT
0437  01001F      492           LD    BC,01FH       ;INIT DES COUNTER
043A  ED434010    493           LD    [CTR1],BC
043E  3A4000      494           LD    A,[INBUF]
0441  EE10        495           XOR   10H           ;TOGGLE BIT 4
0443  324000      496           LD    [INBUF],A
0446  CB67        497           BIT   4,A           ;NOT ON ?
0448  2002        498           JR    NZ,FLB2       ;YES, JP
044A  CB9E        499           RES   3,[HL]
044C  C9          500           RET
044D  CBDE        501  FLB2     SET   3,[HL]
044F  C9          502           RET
                  503  *
0450  ED5B4010    504  EW1ACT   LD    DE,[CTR1]     ;GET COUNT
0454  1B          505           DEC   DE
0455  7A          506           LD    A,D
0456  B3          507           OR    E
0457  201E        508           JR    NZ,STDAT1     ;JP IF NO
0459  DB50        509           IN    A,[EW1]
045B  CB57        510           BIT   2,A           ;ON/OFF EW ACTIVE ?
045D  2807        511           JR    Z,RESET1      ;NO, JP
045F  21001F      512           LD    HL,01FH       ;HERE IF ACTIVE
0462  224010      513           LD    [CTR1],HL     ;RESET COUNT LOOP
0465  C9          514           RET
                  515  *
0466  3A4005      516  RESET1   LD    A,[FLAG5]
0469  CB87        517           RES   0,A
046B  32400F      518           LD    [FLAG5],A
046E  C9          519           RET
                  520  *
046F  ED534010    521  STDAT1   LD    [CTR1],DE     ;RESTORE DATA
0473  C9          522           RET
                  523  *
0474  2A4012      524  EW2ACT   LD    HL,[CTR2]     ;GET COUNT
0477  2B          525           DEC   HL
0478  7C          526           LD    A,H
0479  B5          527           OR    L             ;COUNT ZERO ?
047A  201A        528           JR    NZ,STDAT2     ;JP IF NO
047C  DB50        529           IN    A,[EW1]
047E  CB57        530           BIT   2,A           ;F/W EW ACTIVE ?
0480  2805        531           JR    Z,RESET2      ;NO, JP
0482  21001F      532           LD    HL,01FH
0485  224012      533           LD    [CTR2],HL     ;RESET DES COUNTER
0488  C3020B      534           JP    JOB
                  535  *
```

```
LOCATION OBJECT CODE LINE       SOURCE LINE
048B 3A400F      526 RESET2   LD      A,IFLAGS3
048E CB8F        527          RES     1,A
0490 32400F      528          LD      IFLAGS3,A
0493 C3030B      529          JP      JOB
                 540 *
0496 224012      541 STDAT2   LD      ISTRD,HL    ;RESTORE
0499 C3030B      542          JP      JOB
                 543 *
049C DB40        544 FCWF     IN      A,IFW3
049E CB4F        545          BIT     1,A         ;FW FWD ?
04A0 2008        546          JR      NZ,FSREV    ;JP IF NO
04A2 3A4000      547          LD      A,IINBUF3
04A5 CB5F        548          BIT     3,A         ;DEC MODE ?
04A7 2811        549          JR      Z,RUNMOT    ;JP IF YES
04A9 CBD7        550          SET     2,A         ;SET FWD DIR
04AB 18OD        551          JR      RUNMOT
04AD CB57        552 FSREV    BIT     2,A         ;FW REV ?
04AF 200F        553          JR      NZ,FOF      ;JP IF NO
04B1 3A4000      554          LD      A,IINBUF3
04B4 CB5F        555          BIT     3,A         ;DEC MODE ?
04B6 2802        556          JR      Z,RUNMOT    ;JP IF YES
04B8 CB97        557          RES     2,A         ;SET REV DIR
04BA CBE7        558 RUNMOT   SET     4,A         ;RUN MOT
04BC CBF7        559          SET     6,A         ;FW ON FLG
04BE 1807        560          JR      LDINB
04C0 3A4000      561 FOF      LD      A,IINBUF3
04C3 CBA7        562          RES     4,A         ;STOP MOT
04C5 CBB7        563          RES     6,A         ;FW FLG OFF
04C7 324000      564 LDINB    LD      IINBUF3,A
04CA C9          565          RET
                 566 *
                 567 *** SUBROUTINE TO CONVERT SPEED TO DECIMAL ***
04CB DD214004    568 BINBCD   LD      IX,DISBUF
04CF FD214001    569          LD      IY,SPLB
04D3 AF          570          XOR     A           ;ZERO A REG
04D4 322000      571          LD      I200H3,A
04D7 326000      572          LD      I600H3,A
04DA 324062      573          LD      I40E2H3,A
04DD FD2E00      574          LD      L,IIY+03    ;BIN IN HL
04E0 FD6601      575          LD      H,IIY+13
04E3 01FC18      576          LD      BC,-1000D
04E6 CD04F9      577          CALL   DECND        ;GET MSD
04E9 01FF9C      578          LD      BC,-100D
04EC CD04F9      579          CALL   DECND
04EF 01FFF6      580          LD      BC,-10D
04F2 CD04F9      581          CALL   DECND
04F5 DD7500      582          LD      IIX+03,L    ;STORE LSD
04F8 C9          583          RET
                 584 *
04F9 AF          585 DECND    XOR     A
04FA 5D          586          LD      E,L
04FB 54          587          LD      D,H
04FC 3C          588          INC     A
04FD 09          589          ADD     HL,BC       ;SUBTRACT
04FE DA04FA      590          JP      C,(DECND+1)
0501 6B          591          LD      L,E         ;REMAINDER IN HL
0502 62          592          LD      H,D
0503 3D          593          DEC     A
0504 F5          594          PUSH    AF
0505 2010        595          JR      NZ,NOBLK
0507 3A40E0      596          LD      A,I40E0H3
050A FE00        597          CP      00H
```

```
LOCATION OBJECT CODE LINE       SOURCE LINE
0500 2009            598             JR      NZ,NOBLK
050E F1              599             POP     AF
050F 3E0F            600             LD      A,0FH
0511 DD7700          601             LD      (IX+00),A    ;STORE BLANK
0514 DD23            602             INC     IX
0516 C9              603             RET
0517 F1              604 NOBLK       POP     AF
0518 DD7700          605             LD      (IX+00),A    ;STORE DIGIT
051B 3E01            606             LD      A,01H
051D 324040          607             LD      (40E040),A   ;FLAG
0520 DD23            608             INC     IX
0522 C9              609             RET
                     610
                     611 *** SUBROUTINE TO DISPLAY RPM ***
0523 114004          612 DISP        LD      DE,DISBUF    ;4040
0526 0E00            613             LD      C,EE5
0528 0600            614             LD      B,004
052A 3A4000          615             LD      A,(INBUF3)
052D CB6F            616             BIT     5,A          ;? JOB
052F CA4505          617             JP      Z,NUMER      ;NO,JP
0532 3E00            618             LD      A,0AH        ; "-"
0534 ED79            619             OUT     (C),A
0536 3E1A            620             LD      A,1AH        ; "-"
0538 ED79            621             OUT     (C),A
053A 3E2A            622             LD      A,2AH        ; "-"
053C ED79            623             OUT     (C),A
053E 3E3A            624             LD      A,3AH        ; "-"
0540 ED79            625             OUT     (C),A
0542 C35105          626             JP      STEP
0545 CD8606          627 NUMER       CALL    DIGIT        ;MSD
0548 CD8606          628             CALL    DIGIT
054B CD8606          629             CALL    DIGIT
054E CD8606          630             CALL    DIGIT        ;LSD
0551 CD9005          631 STEP        CALL    SCALE        ;GRAPH SIZE
0554 CD6B06          632             CALL    BARS
0557 3A4003          633             LD      A,(OUTBUF3)
055A 57              634             LD      D,A
055B 3A4000          635             LD      A,(INBUF3)
055E 47              636             LD      B,A
055F E603            637             AND     003H
0561 FE00            638             CP      000          ;LO RPD ?
0563 2008            639             JR      NZ,TREE      ;NO,JP
0565 CBFA            640             SET     7,D          ;LO
0567 CBAA            641             RES     5,D
0569 CBA2            642             RES     4,D
056B 1812            643             JR      LDIT
056D FE02            644 TREE        CP      02           ;MED RPD ?
056F 2008            645             JR      NZ,TEUR      ;NO,JP
0571 CBF2            646             SET     6,D          ;MED
0573 CBAA            647             RES     5,D
0575 CBBA            648             RES     7,D
0577 1806            649             JR      LDIT
0579 CBEA            650 TEUR        SET     5,D          ;HI
057B CBB2            651             RES     6,D
057D CBBA            652             RES     7,D
057F 7A              653 LDIT        LD      A,D
0580 324003          654             LD      (OUTBUF3),A
0583 D360            655             OUT     (LITE3),A
0585 C9              656             RET
                     657 *
0586 3A              658 DIGIT       LD      A,(DE)       ;FETCH BCD
0587 B0              659             OR      B            ;ADR MASK
0588 ED79            660             OUT     (C),A        ;WRITE
```

```
LOCATION OBJECT CODE LINE      SOURCE LINE
0589 13              661              INC     DE
058A 3E10            662              LD      A,10H
058D 80              663              ADD     A,B
058E 47              664              LD      B,A
058F C9              665              RET
                     666      *
0590 3A4000          667 SCALE        LD      A,[INBUF]
0593 E603            668              AND     03H
0595 FE00            669              CP      00H         ;LO RNG ?
0597 2808            670              JR      Z,LDSLR     ;JP IF YES
0599 FE02            671              CP      02H         ;MED RNG ?
059B 2808            672              JR      Z,LDSMR     ;JP IF YES
059D FE01            673              CP      01H         ;HI RNG ?
059F 280E            674              JR      Z,LDSHR     ;YES, JP
05A1 FD2105F0        675              LD      IY,SFR      ;* IF FULL RNG
05A5 1810            676              JR      CHGSPD
05A7 FD2105DE        677 LDSLR        LD      IY,SLR
05AB 180A            678              JR      CHGSPD
05AD FD2105EB        679 LDSMR        LD      IY,SMR
05B1 1804            680              JR      CHGSPD
05B3 FD2105D1        681 LDSHR        LD      IY,SHR
05B7 2A4003          682 CHGSPD       LD      HL,[RPLS]   ;NEW RPM
05BA ED5B4015        683              LD      DE,[OLDRPD] ;OLD RPM
05BE 37              684              SCF
05BF 3F              685              CCF
05C0 ED52            686              SBC     HL,DE       ;SPEED CHG ?
05C2 2808            687              JR      Z,NOCHG     ;JP IF NO
05C4 2A4003          688              LD      HL,[RPLS]
05C7 224015          689              LD      [OLDRPD],HL
05CA FDE9            690              JP      [IY]
05CC 3A4013          691 NOCHG        LD      A,[OLDRDE]
05CF 5F              692              LD      E,A
05D0 C9              693              RET
05D1 110500          694 SHR          LD      DE,1500D    ;HI SPD
05D4 0620            695              LD      B,20H       ;ENTER .062
05D6 DD21A207        696              LD      IX,0A207H
05DA DDE5            697              PUSH    IX
05DC 1825            698              JR      SCALD
05DE 110A00          699 SLR          LD      DE,0750     ;LO SPD
05E1 0620            700              LD      B,20H       ;ENTER .0615
05E3 DD21FC0F        701              LD      IX,0FC0FH
05E7 DDE5            702              PUSH    IX
05E9 181B            703              JR      SCALD
05EB 110500          704 SMR          LD      DE,500D     ;MED SPD
05EE 0620            705              LD      B,20H       ;ENTER .05
05F0 DD21EEEE        706              LD      IX,0EEEEH
05F4 DDE5            707              PUSH    IX
05F6 180B            708              JR      SCALD
05F8 110A00          709 SFR          LD      DE,0750     ;FULL SPD
05FB 0620            710              LD      B,20H       ;ENTER .008
05FD DD218729        711              LD      IX,0B729H
0601 DDE5            712              PUSH    IX
0603 37              713 SCALD        SCF
0604 3F              714              CCF
0605 ED52            715              SBC     HL,DE
0607 EB              716              EX      DE,HL
0608 CD0000          717              CALL    FLOT        ;IN D-E
060B E1              718              POP     HL          ;IN B-H-L
060C CD0000          719              CALL    FMPY        ;MULTIPLY
060F CD0000          720              CALL    FIXX        ;RESULT IN E
0612 1C              721              INC     E
0613 7B              722              LD      A,E
0614 324013          723              LD      [OLDRDE],A
```

```
LOCATION OBJECT CODE LINE      SOURCE LINE
0617 C9           724              RET
                  725  *
0618 2A400E       726  BARG        LD    A,(GRAPH+23)
061B F5           727              PUSH  AF
061C 21420D       728              LD    HL,GRAPH
061F 3EFF         729              LD    A,0FFH      ;BEEP OFF
0621 0620         730              LD    B,020
0623 77           731  CBR         LD    (HL),A
0624 23           732              INC   HL
0625 05           733              DEC   B
0626 20FB         734              JR    NZ,CBR
0628 21420D       735              LD    HL,GRAPH
062B 0608         736  BEEG        LD    B,08H       ;BIT COUNTER
062D 1D           737  NXT         DEC   E
062E FA0629       738              JP    M,BHOW
0631 CB26         739              SLA   (HL)
0633 05           740              DEC   B
0634 20F7         741              JR    NZ,NXT
0636 23           742              INC   HL          ;NEXT LOC.
0637 18F2         743              JR    BEEG
0639 21420D       744  BHOW        LD    HL,GRAPH
063C 7E           745              LD    A,(HL)
063D D330         746              OUT   (AR13),A
063F 23           747              INC   HL
0640 7E           748              LD    A,(HL)
0641 D320         749              OUT   (AR23),A
0643 23           750              INC   HL
0644 7E           751              LD    A,(HL)
0645 E60F         752              AND   0FH
0647 47           753              LD    B,A
0648 F1           754              POP   AF
0649 E6F0         755              AND   0F0H
064B B0           756              OR    B
064C 32400E       757              LD    (GRAPH+23),A
064F D320         758              OUT   (AR23),A
0651 C9           759              RET
                  760
                  761  *** SUBROUTINE FOR TIME DELAYS ***
0652 D9           762  WAIT        EXX
0653 08           763              EX    AF,AF'
0654 FDE5         764              PUSH  IY
0656 D1           765              POP   DE
0657 1B           766  LOOP        DEC   DE
0658 7A           767              LD    A,D
0659 320040       768              LD    (20040),A
065C 320040       769              LD    (20040),A
065F B3           770              OR    E
0660 20F5         771              JR    NZ,LOOP
0662 D9           772              EXX
0663 08           773              EX    AF,AF'
0664 C9           774              RET
                  775
                  776  *** SUBROUTINE TO START MOTOR ***
0665 2A4001       777  RUN         LD    HL,(SPLED)  ;FETCH SPEED
0668 EB           778              EX    DE,HL
0669 CD0000       779              CALL  FLOT        ;IN C-D-E
066C 3A4200       780              LD    A,(INBUF3)
066F E603         781              AND   03H
0671 FE00         782              CP    00H         ;FULL SPD?
0673 2804         783              JR    Z,CFW       ;YES,JP
0675 FE01         784              CP    01H         ;HI SPD?
0677 2820         785              JR    Z,CFW       ;YES,JP
```

```
LOCATION OBJECT CODE LINE      SOURCE LINE
0675 FE02        786             CP      02H             ;MED SPD ?
067B 2814        787             JR      Z,CRV           ;YES,JP
                 788     ; snower    V = 0.095X-1.12
067D 0620        789             LD      B,20H           ;ENTER 0.095
067F 21D82F      790             LD      HL,02D8FH
0682 CD0000      791             CALL    FMPY
0685 CD0000      792             CALL    FIXX            ;IN DE
0688 210001      793             LD      HL,01D
068B EB          794             EX      DE,HL
068C ED52        795             SBC     HL,DE
068E 5D          796             LD      E,L             ;RESULT IN E
068F 182A        797             JR      VCAL
                 798     ; regector  V = .095X-1.5
0691 0620        799 CRV         LD      B,20H           ;ENTER .095
0693 21C02F      800             LD      HL,02FC0H
0696 CD0000      801             CALL    FMPY
0699 CD0000      802             CALL    FIXX            ;RESULT IN E
069C 210001      803             LD      HL,01D
069F EB          804             EX      DE,HL
06A0 ED52        805             SBC     HL,DE
06A2 5D          806             LD      E,L
06A3 1820        807             JR      VCAL
                 808     ; burn      V = .111X-21.5
06A5 0620        809 CBW         LD      B,20H           ;ENTER .111
06A7 21E352      810             LD      HL,0E352H
06AA CD0000      811             CALL    FMPY
06AD CD0000      812             CALL    FIXX            ;IN E
06B0 21001E      813             LD      HL,22D
06B3 EB          814             EX      DE,HL
06B4 ED52        815             SBC     HL,DE
06B6 5D          816             LD      E,L
06B7 1812       817             JR      VCAL
                 818 ;FULL SPD RANGE V = .102X-1.72
06B9 0620        819 CFV         LD      B,20H           ;ENTER .102
06BB 21DEF1      820             LD      HL,0D2F1H
06BE CD0000      821             CALL    FMPY
06C1 CD0000      822             CALL    FIXX            ;RESULT IN DE
06C4 210002      823             LD      HL,02
06C7 EB          824             EX      DE,HL
06C8 ED52        825             SBC     HL,DE
06CA 5D          826             LD      E,L
06CB 3A4000      827 VCAL        LD      A,[INBUF3
06CE CB6F        828             BIT     5,A             ;? JOG MODE
06D0 2051        829             JR      NZ,VCM          ;JP IF YES
06D2 CD672A      830             CALL    DIRCHG
06D5 CBD7        831             SET     2,A             ;SET RUN
06D7 324002      832             LD      [OUTBUF3,A
06DA D3E0        833             OUT     [LITE3,A        ;MOTOR ON
06DC 7B          834             LD      A,E
06DD D320        835             OUT     [DAC3,A         ;VELOCITY
06DF 3A4000      836             LD      A,[INBUF3
06E2 32401D      837             LD      [OLDINB3,A
06E5 CB6F        838             BIT     5,A             ;?DEC
06E7 2809        839             JR      Z,DEC           ;YES,JP
06E9 3A400F      840             LD      A,[FLAGS3
06EC CB97        841             RES     2,A
06EE 32400F      842             LD      [FLAGS3,A
06F1 C9          843             RET
06F2 3A400F      844 DEC         LD      A,[FLAGS3
06F5 CB57        845             BIT     2,A             ;DEC TIMER ACTV ?
06F7 2003        846             JR      NZ,DECTIM
06F9 CBD7        847             SET     2,A
```

```
LOCATION OBJECT CODE LINE         SOURCE LINE
06FB 324025      848              LD    IFLAGS3,A
06FE 210055      849              LD    HL,0055H
0701 224014      850              LD    ICTR20,HL
0704 ED5B4014    851 DECTIM       LD    DE,ICTR20    ;GET COUNT
0708 1B          852              DEC   DE
0709 7A          853              LD    A,D
070A 83          854              OR    E
070B 2011        855              JR    NZ,STDAT2
070D 3A4000      856              LD    A,IINBUF3
0710 EE04        857              XOR   04H          ;FLIP FWD/REV
0712 324000      858              LD    IINBUF3,A
0715 3A400F      859              LD    A,IFLAGS3
0718 CB97        860              RES   2,A
071A 32400F      861              LD    IFLAGS3,A
071D C9          862              RET
071E ED534014    863 STDAT2       LD    ICTR20,DE    ;SAVE COUNT
0722 C9          864              RET
0723 3A4000      865 WCM          LD    A,IINBUF3    ;* IF JOG MODE
0726 CB67        866              BIT   4,A          ;? RUN
0728 C8          867              RET   Z
0729 3E01        868              LD    A,01H
072B D320        869              OUT   IDAC3,A
072D 3A4002      870              LD    A,IOUTBUF3
0730 CB97        871              RES   2,A          ;NOT START BIT
0732 CBCF        872              SET   1,A          ;SET FWD LITE
0734 324002      873              LD    IOUTBUF3,A
0737 D360        874              OUT   ILITE3,A     ;START
0739 C9          875              RET
                 876 *
073A FD2102FF    877 DIRCHG       LD    IY,02FFH
073E 214002      878              LD    HL,IWBUF
0741 3A401D      879              LD    A,IOLDINB3
0744 47          880              LD    B,A
0745 3A4002      881              LD    A,IOUTBUF3
0748 CB56        882              BIT   2,IHL        ;REV THIS TIME ?
074A 280F        883              JR    Z,REVDIR     ;JP IF YES
074C CB50        884              BIT   2,B          ;FWD LAST TIME ?
074E 2022        885              JR    NZ,SET1      ;JP IF YES
0750 CB97        886              RES   2,A          ;MOTOR OFF
0752 D360        887              OUT   ILITE3,A
0754 CD6562      888              CALL  WAIT
0757 CBCF        889              SET   1,A          ;SET FWD
0759 1800        890              JR    DEL2
075B CB50        891 REVDIR       BIT   2,B          ;REV LAST TIME ?
075D 281E        892              JR    Z,REB1       ;JP IF YES
075F CB97        893              RES   2,A          ;MOTOR OFF
0761 D360        894              OUT   ILITE3,A
0763 CD6562      895              CALL  WAIT
0766 CBCF        896              RES   1,A          ;SET REV
0768 D360        897 DEL2         OUT   ILITE3,A
076A FD210010    898              LD    IY,0010H
076E CD6562      899              CALL  WAIT
0771 C9          900              RET
0772 CBCF        901 SET1         SET   1,A          ;FWD DIR
0774 C9          902              RET
0775 CBBF        903 REB1         RES   1,A          ;REV DIR
0777 C9          904              RET
                 905 *
                 906 *** SUBROUTINE TO TEST LITES AND DIGITS ***
0778 328000      907 CHECK        LD    I8000H,A
077B 32A000      908              LD    IA000H,A
077E 3E0C        909              LD    A,0CH
```

| LOCATION | OBJECT CODE | LINE | SOURCE LINE | | |
|---|---|---|---|---|---|
| 0780 | 324800 | 910 | LD | (INBUF0),A | |
| 0783 | 3EED | 911 | LD | A,0EDH | |
| 0785 | 324801 | 912 | LD | (BPL80),A | |
| 0788 | AF | 913 | XOR | A | |
| 0789 | 324802 | 914 | LD | (BP480),A | |
| 078C | 3E08 | 915 | LD | A,08H | |
| 078E | D3E0 | 916 | OUT | (LITE0),A | |
| 0790 | 3E2F | 917 | LD | A,02FH | |
| 0792 | 324808 | 918 | LD | (GRAPH80),A | |
| 0795 | D382 | 919 | OUT | (BAR80),A | |
| 0797 | 3E0F | 920 | LD | A,0FH | |
| 0799 | CD087A | 921 | CALL | DISOUT | |
| 079C | 114004 | 922 | LD | DE,DISBUF | |
| 079F | CD01B0 | 923 | CALL | DIGITS | |
| 07A2 | 1E00 | 924 | LD | E,00H | |
| 07A4 | CD061B | 925 | CALL | BARS | |
| 07A7 | CD0667 | 926 | CALL | DELAY | |
| 07AA | 3E06 | 927 | LD | A,REVLEV | |
| 07AC | 324807 | 928 | LD | (DISBUF+20),A | |
| 07AF | CD087D | 929 | CALL | (DISOUT+2) | |
| 07B2 | CD0667 | 930 | CALL | DELAY | |
| 07B5 | CD0667 | 931 | CALL | DELAY | |
| 07B8 | CD0667 | 932 | CALL | DELAY | |
| 07BB | CD0667 | 933 | CALL | DELAY | |
| 07BE | 3E08 | 934 | LD | A,08H | |
| 07C0 | CD087A | 935 | CALL | DISOUT | |
| 07C3 | CD0667 | 936 | CALL | DELAY | |
| 07C6 | 3E0F | 937 | LD | A,0FH | ;BLANKS TO DISPLAY |
| 07C8 | CD087A | 938 | CALL | DISOUT | |
| 07CB | 3E08 | 939 | LD | A,08H | ;B'B TO DSPLY BUF |
| 07CD | CD08EF | 940 | CALL | FILBUF | |
| 07D0 | 0E00 | 941 | LD | C,BEB2 | ;B'B IN RPM LO |
| 07D2 | 0640 | 942 | LD | B,40H | |
| 07D4 | 210004 | 943 | LD | HL,04H | |
| 07D7 | 114004 | 944 | LD | DE,DISBUF | |
| 07DA | CD01B2 | 945 | CALL | NXTDIS | |
| 07DD | CD0667 | 946 | CALL | DELAY | |
| 07E0 | 3E0F | 947 | LD | A,0FH | ;BLANK RPM LO |
| 07E2 | CD08EF | 948 | CALL | FILBUF | |
| 07E5 | 0E00 | 949 | LD | C,BEB2 | |
| 07E7 | 0640 | 950 | LD | B,040H | |
| 07E9 | 210004 | 951 | LD | HL,04H | |
| 07EC | 114004 | 952 | LD | DE,DISBUF | |
| 07EF | CD01B2 | 953 | CALL | NXTDIS | |
| 07F2 | 1E14 | 954 | LD | E,20D | ;DSPLY BAR GRAPH |
| 07F4 | CD061B | 955 | CALL | BARS | |
| 07F7 | CD0667 | 956 | CALL | DELAY | |
| 07FA | 1E00 | 957 | LD | E,00H | |
| 07FC | CD061B | 958 | CALL | BARS | |
| 07FF | 3E08 | 959 | LD | A,08H | ;B'B TO DSPLY BUF |
| 0801 | CD08EF | 960 | CALL | FILBUF | |
| 0804 | 0E00 | 961 | LD | C,BEB2 | ;B'B TO RPM HI |
| 0806 | 0600 | 962 | LD | B,00H | |
| 0808 | 210004 | 963 | LD | HL,04H | |
| 080B | 114004 | 964 | LD | DE,DISBUF | |
| 080E | CD01B3 | 965 | CALL | NXTDIS | |
| 0811 | CD0667 | 966 | CALL | DELAY | |
| 0814 | 3E0F | 967 | LD | A,0FH | ;BLANK DSPLY BUF |
| 0816 | CD08EF | 968 | CALL | FILBUF | |
| 0819 | 0E00 | 969 | LD | C,BEB2 | |
| 081B | 0E70 | 970 | LD | B,00H | |
| 081D | 210004 | 971 | LD | HL,04H | |
| 0820 | 114004 | 972 | LD | DE,DISBUF | |
| 0823 | CD01B3 | 973 | CALL | NXTDIS | |

```
LOCATION OBJECT CODE LINE       SOURCE LINE
0B1B 3EB0                974         LD      A,0B0H          ;DSPLY LO
0B2B D2E0                975         OUT     (LITE3),A
0B2A CD0B67              976         CALL    DELAY
0B2D 3E40                977         LD      A,40H           ;DSPLY MED
0B2F D2E0                978         OUT     (LITE3),A
0B31 CD0B67              979         CALL    DELAY
0B34 3E20                980         LD      A,20H           ;DSPLY HI
0B36 D2E0                981         OUT     (LITE3),A
0B38 CD0B67              982         CALL    DELAY
0B3B 3E0A                983         LD      A,0AH           ;DSPLY FWD
0B3D D2E0                984         OUT     (LITE3),A
0B3F CD0B67              985         CALL    DELAY
0B42 3E1A                986         LD      A,1AH           ;DSPLY FTEN
0B44 D2E0                987         OUT     (LITE3),A
0B46 CD0B67              988         CALL    DELAY
0B49 3E1F                989         LD      A,01FH
0B4B D2B0                990         OUT     (BAR3),A        ;DSPLY NORM & CONT
0B4D CD0B67              991         CALL    DELAY
0B50 3E02                992         LD      A,02H
0B52 D2E0                993         OUT     (LITE3),A       ;AUDIO ON
0B54 CD0B67              994         CALL    DELAY
0B57 3E0A                995         LD      A,0AH           ;AUDIO OFF
0B59 D2E0                996         OUT     (LITE3),A
0B5B 110B91              997         LD      DE,LORNG
0B5E CD015D              998         CALL    DIGITB
0B61 3E0A                999         LD      A,0AH
0B63 240002              1000        LD      (OUTBUF3),A
0B66 C9                  1001        RET
                         1002 *
0B67 FD217FFF            1003 DELAY  LD      IY,07FFFH
0B6B CD0B52              1004        CALL    WAIT
0B6E C9                  1005        RET
                         1006 *
0B6F 214204              1007 FILBUF LD      HL,DIGBUF
0B72 0609                1008        LD      B,09H
0B74 05                  1009 BEV    DEC     B
0B75 C8                  1010        RET     Z
0B76 77                  1011        LD      (HL),A
0B77 23                  1012        INC     HL
0B78 18FA                1013        JR      BEV
                         1014 *
0B7A CD0B6F              1015 DIGOUT CALL    FILBUF
0B7D 114204              1016        LD      DE,DIGBUF
0B80 0E00                1017        LD      C,00
0B82 0604                1018        LD      B,04H
0B84 CD05BE              1019        CALL    DIGIT
0B87 CD05BE              1020        CALL    DIGIT
0B8A CD05BE              1021        CALL    DIGIT
0B8D CD05BE              1022        CALL    DIGIT
0B90 C9                  1023        RET
                         1024 *
                         1025 *DATA CONSTANTS
                         1026 *
0B91 0F                  1027 LORNG  DEFB    0FH
0B92 04                  1028        DEFB    04H
0B93 00                  1029        DEFB    00H
0B94 00                  1030        DEFB    00H
0B95 05                  1031        DEFB    05H
0B96 07                  1032        DEFB    07H
0B97 0F                  1033        DEFB    0FH
0B98 0F                  1034        DEFB    0FH
0B99 0F                  1035 MIDRNG DEFB    0FH
```

What is claimed is:

1. An electrically drive surgical apparatus comprising:
   an elongated, autoclavable, hollow handpiece having a generally cylindrical configuration;
   a rotatably drivable cutting blade assembly;
   a motor disposed in said handpiece;
   securing means for engaging said cutting blade to said handpiece to be rotatably driven by said motor; and
   a switch cluster disposed on said handpiece and including at least a first switch means for selectively actuating and deactuating said motor and at least a second switch means for selectively changing the operating speed of said motor, said switch cluster being arcuately configured to substantially conform to the configuration of said handpiece, said switch cluster including a plurality of pushbuttons and a printed circuit board having pairs of switch contacts positioned to be conductively bridged upon depression of respective pushbuttons, said printed circuit board having an arcuate configuration to match the configuration of said handpiece, said printed circuit board being capable of withstanding temperatures in excess of 270° F. without adverse effect.

2. The apparatus according to claim 1 wherein said printed circuit board comprises a metal plate coated on both surfaces with porcelain and having electrically conductive leads defined on at least one of said porcelain-coated surfaces.

3. The apparatus according to claim 2 wherein said arcuate configuration has a radius of curvature in the range of 0.6 to 0.7 inches.

4. In an electrically drive surgical apparatus including an elongate, autoclavable handpiece having a forward end, an electric motor disposed in said handpiece and operable to rotate in forward and reverse directions at varying speeds, and an arthroscopic cutting blade received in said forward end of said handpiece to be rotatably driven by said motor and extending longitudinally from said handpiece, an improved motor control arrangement comprising:

a cluster of first, second, third and fourth manually-operable pushbutton switches disposed on said handpiece at said forward end;

first control means, including said first switch, for selectively controlling the forward or reverse direction in which said motor drives said cutting blade;

second control means, including said second switch, for selectively increasing the speed at which said motor drives said cutting blade;

third control means, including said third switch, for selectively decreasing the speed at which said motor drives said cutting blade; and fourth control means, including said fourth switch, for selectively activating and deactivating said motor;

said handpiece having a longitudinal dimension and a perimetric dimension extending transversely to said longitudinal dimension, said first, second and third pushbutton switches being disposed in spaced alignment along said perimetric dimension of said handpiece, and said fourth pushbutton switch being more elongated along said perimetric dimension than each of said first, second and third switches and being spaced from and longitudinally aligned with said first, second and third switches;

wherein said first, second, third and fourth control means comprise circuit-carrying means disposed within said handpiece and carrying at least four pairs of switch contacts positioned to be bridged upon actuation of said first, second, third and fourth switches, respectively;

wherein each of said first, second and third switches includes: a resilient dome-like member tapering from an open first end having a relatively large periphery to a closed second end having a relatively small periphery, said closed second end being disposed in substantial registration with a respective pair of three of said pairs of contacts on said circuit-carrying means; and an electrically conductive member secured to said second end so as to electrically bridge said respective pair of contacts when said second end is pressed a predetermined distance toward said circuit-carrying means; and wherein said fourth switch includes: a resilient transversely elongated dome-like member tapering from an open end to a closed actuation end, said actuation end being disposed in substantial registration with a fourth pair of said contacts on said circuit-carrying means; and a plurality of transversely spaced electrically conductive members secured to the actuator end so as to individually electrically bridge said fourth pair of contacts when a corresponding portion of said actuator end is pressed a predetermined distance toward said circuit-carrying means.

5. The apparatus according to claim 4 wherein said plurality of transversely spaced electrically conductive members are three in number, each being longitudinally aligned along the length dimension of said handpiece with the electrically conductive member of a respective one of said first, second and third switches.

6. The apparatus according to claim 4 wherein said handpiece is generally cylindrical, wherein said spaced alignment extends arcuately along the circumference of said handpiece, and wherein said circuit-carrying means is an arcuate printed circuit board configured as a segment of a cylinder and disposed inside said handpiece in closely spaced relation to said first, second third and fourth switches.

7. The apparatus according to claim 4 further comprising:

an integral sheet of flexible non-conductive material, said resilient dome-like members of all of said first, second, third and fourth switches being part of said integral sheet;

a plate overlying said integral sheet and having a plurality of apertures defined therethrough, said apertures being positioned in alignment with respective ones of said first, second, third and fourth switches such that the dome-like member of each switch projects through a respective aperture in said plate; and wherein said circuit-carrying means is a printed circuit board.

8. The apparatus according to claim 7 wherein said handpiece has a generally cylindrical portion, and wherein said integral sheet, said plate and said printed circuit board are each segments of a cylinder.

9. An electrically driven surgical apparatus according to claim 1 wherein said handpiece includes sensing means and said cutting blade assembly includes an elongate tubular outer member having a distal end with an opening therein and a proximal end, an elongate inner member received in said outer member and having a distal cutting end disposed adjacent said opening in said distal end of said outer member and a proximal end rotatably driven by said motor to rotate in said outer member and a plastic hub mounted on said proximal end of said outer member including first and second sections, at least one of said first and second sections having recess means therein, coding means disposed in said recess means having a characteristic detectable by said sensing means, said first and second sections being secured together to hold said coding means in said recess means whereby said cutting blade assembly can be identified by the sensing means in said handpiece detecting the presence of said coding means.

* * * * *

UNITED STATES PATENT AND TRADEMARK OFFICE
CERTIFICATE OF CORRECTION

PATENT NO. : 5,217,478
DATED : June 8, 1993
INVENTOR(S) : Fred Rexroth

It is certified that error appears in the above-identified patent and that said Letters Patent is hereby corrected as shown below:

Column 1, line 61, delete "ar" and replace with --are--.

Column 8, line 22, delete "ca" and replace with --can--.

Column 10, line 1, delete "speed range".

Column 12, line 52, delete "TELFON" and replace with --TEFLON--.

Column 16, line 4, delete "ar" and replace with --are--.

Column 17, line 49, delete "4".

Column 61, line 51, delete "drive" and replace with --driven--.

Column 62, line 65, delete "drive" and replace with --driven--.

Column 63, line 43, delete "insubstantial" and replace with --in substantial--.

Signed and Sealed this

Fifth Day of July, 1994

Attest:

BRUCE LEHMAN

Attesting Officer  Commissioner of Patents and Trademarks